US008975387B1

(12) United States Patent
Venditti et al.

(10) Patent No.: US 8,975,387 B1
(45) Date of Patent: Mar. 10, 2015

(54) MODIFIED CARBOHYDRATE-CHITOSAN COMPOUNDS, METHODS OF MAKING THE SAME AND METHODS OF USING THE SAME

(75) Inventors: Richard A. Venditti, Raleigh, NC (US); Joel J. Pawlak, Raleigh, NC (US); Abdus Salam, Raleigh, NC (US); Khaled Fathy El-Tahlawy, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 519 days.

(21) Appl. No.: 13/052,463

(22) Filed: Mar. 21, 2011

Related U.S. Application Data

(60) Provisional application No. 61/316,311, filed on Mar. 22, 2010.

(51) Int. Cl.
*C08B 37/08* (2006.01)
*C08B 37/00* (2006.01)
*C08B 31/00* (2006.01)
*C08B 31/14* (2006.01)
*A61K 31/732* (2006.01)
*A61K 31/718* (2006.01)

(52) U.S. Cl.
USPC .......... 536/20; 536/102; 536/106; 536/123.1; 514/55; 514/60; 514/54

(58) Field of Classification Search
USPC ........ 536/20, 102, 106, 123.1; 514/55, 60, 54
See application file for complete search history.

(56) References Cited

U.S. PATENT DOCUMENTS

| | | | |
|---|---|---|---|
| 4,111,810 A | 9/1978 | Arai et al. | |
| 5,130,391 A | 7/1992 | Ahmed et al. | |
| 5,216,098 A | 6/1993 | Ahmed et al. | |
| 5,252,690 A | 10/1993 | Ahmed et al. | |
| 5,286,827 A | 2/1994 | Ahmed | |
| 5,314,420 A | 5/1994 | Smith et al. | |
| 5,451,613 A | 9/1995 | Smith et al. | |
| 5,462,972 A | 10/1995 | Smith et al. | |
| 5,599,916 A | 2/1997 | Dutkiewicz et al. | |
| 5,958,589 A | 9/1999 | Glenn et al. | |
| 6,867,287 B2* | 3/2005 | Carlucci et al. | 536/20 |
| 7,560,419 B2 | 7/2009 | Fang et al. | |
| 7,833,384 B2 | 11/2010 | Weerawarna | |
| 7,959,762 B2 | 6/2011 | Weerawarna | |
| 8,163,309 B2 | 4/2012 | Glenn et al. | |
| 8,545,691 B2 | 10/2013 | Teymour et al. | |
| 2003/0027787 A1* | 2/2003 | Couture et al. | 514/54 |
| 2006/0045912 A1* | 3/2006 | Truog | 424/468 |
| 2006/0062990 A1 | 3/2006 | Gotoh | |
| 2007/0110962 A1* | 5/2007 | Tien et al. | 428/156 |
| 2007/0179291 A1 | 8/2007 | Thibodeau et al. | |
| 2008/0082067 A1 | 4/2008 | Weerawarna et al. | |
| 2008/0226722 A1* | 9/2008 | Van Tomme et al. | 424/486 |
| 2010/0057027 A1 | 3/2010 | Furno et al. | |
| 2011/0183380 A1 | 7/2011 | El-Tahlawy et al. | |

FOREIGN PATENT DOCUMENTS

| | | |
|---|---|---|
| EP | 1 649 851 | 4/2006 |
| WO | WO 2004/085481 | 10/2004 |
| WO | WO 2006/032929 | 3/2006 |
| WO | WO 2006/037157 | 4/2006 |
| WO | WO 2006/042364 | 4/2006 |
| WO | WO 2010/148357 | 12/2010 |
| WO | 2012/097447 A2 | 7/2012 |

OTHER PUBLICATIONS

Alonso, D., et al. 2009 Cross-linking chitosan into UV-irradiated cellulose fibers for the preparation of antimicrobial-finished textiles. Carbohydrate Polymer 77(3),536-543.
Bernabél, P. et al. 2005 Swelling behavior of chitosan/pectin polyelectrolyte complex membranes. Effect of thermal cross-linking, Polymer Bulletin, 55, 367-375.
Christian, D. et al. 2008 Novel superabsorbent cellulose-based hydrogels crosslinked with citric acid. Applied Polymer Science, 110 (4) 2453-2460.
Edlund, U. 2008 A Microspheric System: Hemicellulose-based Hydrogels. Bioactive and Compatible Polymers, 23(2), 171-186.
El-Tahlawy Khaled F., et al. 2005 The antimicrobial activity of cotton fabrics treated with different crosslinking and chitosan. Carbohydrate Polymer, 60 421-430.
El-Tahlawy, K. et al. 2007 Carbohydrate Polymers, 67(3), 319-331.
Gabrielii, L, & Gatenholm, P. 1998 Preparation and properties of hydrogels based on hemicellulose. Applied Polymer Science, 69, 1661-1667.
Gabrielii, I. et al. 2000 Separation, characterization and hydrogel-formation of hemicellulose from aspen wood. Carbohydrate Polymers, 43(4), 367-374.
Helander, I.M., et al. 2001 Chitosan disrupts the barrier properties of the outer membrane of Gram-negative bacteria. Intl J of Food Microbiology, 71(2), 235-244.
Lee K. Y., W. H. Park, W. S. Ha, 1997 Polyelectrolyte Complexes of Sodium Alginate with Chitosan or Its Derivatives for Microcapsules J. Appl. Polym. Sci., 63, 425-432.

(Continued)

*Primary Examiner* — Shaojia Anna Jiang
*Assistant Examiner* — Michael C Henry
(74) *Attorney, Agent, or Firm* — Olive Law Group, PLLC; Nathan P. Letts

(57) ABSTRACT

Compositions of matter are provided that include chitosan and a modified carbohydrate. The modified carbohydrate includes a carbohydrate component and a cross linking agent. The modified carbohydrate has increased carboxyl content as compared to an unmodified counterpart carbohydrate. A carboxyl group of the modified carbohydrate is covalently bonded with an amino group of chitosan. The compositions of matter provided herein may include cross linked starch citrate-chitosan and cross linked hemicellulose citrate-chitosan, including foams thereof. These compositions yield excellent absorbency and metal chelation properties. Methods of making cross linked modified carbohydrate-chitosan compounds are also provided.

40 Claims, 20 Drawing Sheets

(56) References Cited

OTHER PUBLICATIONS

Lim, S.H. and Hudsen, S.M. 2004 Synthesis and antimicrobial activity of a water-soluble chitosan derivative with a fiber-reactive group. Carbohydrate Research, 339, 313-319.
Lim, Sang-Hoon; Hudson, Samuel M. 2004 Carbohydrate Polymers, 56(2), 227-234.
Lindblad, M. S., et al. 2004 New hemicellulose-based hydrogels. ACS Symposium Series, 864 (Hemicelluloses), 347-359.
Liu, H., Du, Y. Yang, J. and Zhu, H. 2004 Structural characterization and antimicrobial activity of chitosan/betain derivative complex. Carbohydrate polymers, 55, 291-297.
15. Liu, X.F., Guan, Y.L., Yang, D.Z., Li, Z. and Yao, K.D. 2001 Antimicrobial action of chitosan and carboxymethylated chitosan. J. Appl. Polymer Sci. 29, 1324-1335.
Petzold, K., Schwikal, K., & Heinze, T. 2006 Carboxymethyl xylan-synthesis and detailed structure characterization. Carbohydrate Polymers, 64(2), 292-298.
Rajesh, K. J., Markku ,S., & Wolfgang, G. G. 2001 Thermoplastic Xylan Derivatives with Propylene Oxide. Cellulose 7(4), 319-336.
Robert, E., & Wing P.1996 Starch Citrate preparation and Ion Exchange Properties, Starch/Starke 48, 7/8. S 275-279.
Rui, S., et al. 2007 Characterization of citric acid/glycerol co-plasticized thermoplastic starch prepared by melt blending. Carbohydrate Polymers, 69(4), 748-755.
Thatte, R.M. PhD Dissertationi 2004 Synthesis and antibacterial assessment of water-soluble hydrophobic chitosan derivatives bearing quaternary ammonium functionality (online version).
Umemura, K. ,Kawai, S. 2008 Preparation and characterization of maillard reacted chitosan films with hemicellulose model compounds. Applied Polymer Science, 108(4), 2481-2487.
Vaara, M. and Vaara, T. 1983 Polycations as outer membrane-disorganizing agents. Antimicrobiology agents Chemotherapeutant, 24, 114-122.
Vaca-Garcia, C. et al 1998 Cellulose esterification with fatty acids and acetic anhydride in lithium chloride/N, N-dimethylacetamide medium. Am Oil Chemists' Soc, 75(2), 315-319.
Wang, X., Du, Y. and Liu, H. 2004 Preparation, characterization and antimicrobial activity of chitosan Zn complex. Carbohydrate Polymers, 56, 21-26.
Xaio, F. S., et al. 2003 Preparation of sugarcane bagasse hemicellulosic succinates using NBS as a catalyst. Carbohydrate Polymers 53(4), 1 483-495.
Yin, J., Kun, K.L., Chen, X., Khutoryanskiy, V.V. 2006 Miscibility studies of the blends of chitosan with some cellulose ethers. Carbohydrate Polymers, 63(2), 238-244.
Zhang, C., Ping, Q., Zhang, H., Shen, J. European Polymer Journal, 2003, 39, 1629-1634.
Zhang, G., Xie, S., Guo, Y., Lu, F. 2002 Chitosan-acrylamide graft copolymers and flocculation properties. Xi'an Jiaotong Daxue Xuebao, 36(5), 541-544.
Zheng, L.Y. and Zhu, J.F. 2003 Study on antimicrobial activity of chitosan with different molecular weights. Carbohydrate Polymers, 54, 527-530.
Demitri et al.; Novel Superabsorbent Cellulose-Based Hydrogels Crosslinked with Citric Acid; Journal of Applied Polymer Science 2008; 110: 2453-2460.
Gaffar, Mohammed A.; Preparation and Utilization of New Carboxyl Group Containing Cation Exchangers Based on Starch Using a Dry Reaction Method; Starch/Stärke; 2002; 54:185-192.
Heinze et al.; Starch derivatives of high degree of functionalization 9: carboxymethyl starches; Cellulose; 2004; 11: 239-245.
Kiatkamjornwong, Suda; Superabsorbent Polymers and Superabsorbent Polymer Composites; ScienceAsia; 2007; Supplement 1: 39-43.
Kumar, Majeti N. V. Ravi; A review of chitin and chitosan applications; Reactive & Functional Polymers 2000; 46: 1-27.
Okazaki et al.; Development of Poly(vinyl alcohol) Hydrogel for Waste Water Cleaning. II. Treatment of N,N-Dimethylformamide in Waste Water with Poly(vinyl alcohol) Gel with Immobilized Microorganisms; Journal of Applied Polymer Science; 1995; 58: 2243-2249.
Rozie et al.; Crosslinked xylan as an affinity adsorbent for endo-xylanases; Carbohydrate Polymers; 1992; 17: 19-28.
Varma et al.; Metal complexation by chitosan and its derivatives: a review; Carbohydrate Polymers; 2004; 55: 77-93.
Wing et al.; Starch Citrate: Preparation and Ion Exchange Properties; Starch/Stärke;1996; 48:275-279.
Pelissari et al., Extrusion parameters related to starch/citosan active films properties; International Journal of Food Science and Technology 2011, 46, 702-710.
Baran et al., Starch-chitosan hydrogels prepared by reductive alkylation cross-linking, Journal of Materials Science: Materials in Medicine 15 (2004) 759-765.
Yu et al., Polymer blends and composites from renewable resources, Prog. Polym. Sci. 31 (2006) 576-602.
Liu et al., Thermal processing of starch-based polymers, Progress in Polymer Science 34 (2009) 1348-1368.
Rayford et al, Crosslinked Cationic and anionic Starches: Preparaton and Use in Heavy Metal Removal; Starch/Starke 31 (1979) Nr. 11, S. 361-365.

* cited by examiner

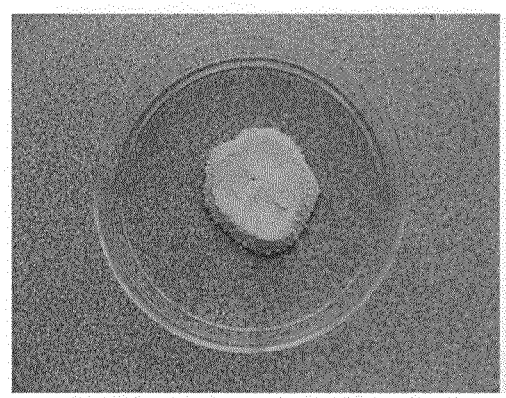 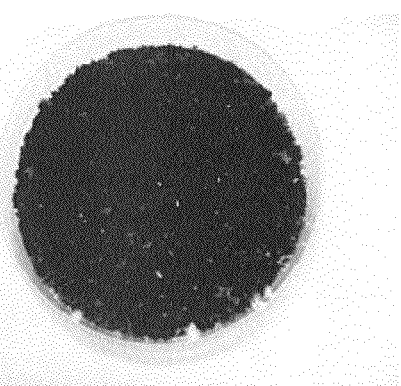
Fig. 1A   Fig. 1B
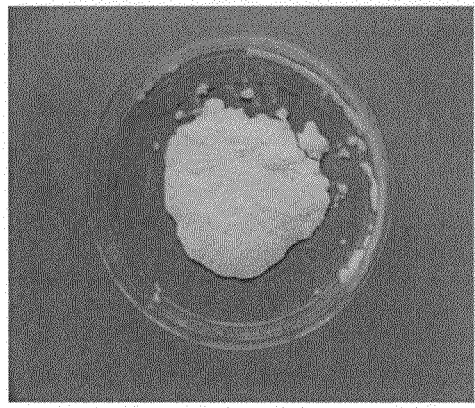 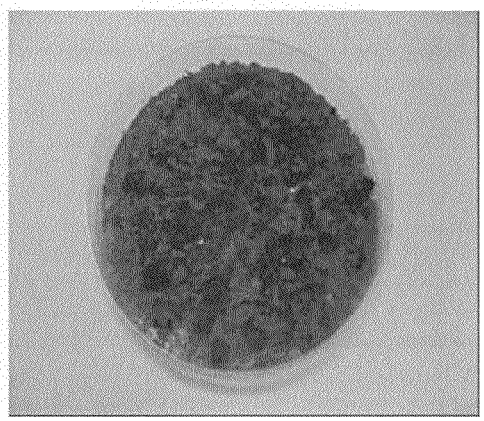
Fig. 1C   Fig. 1D

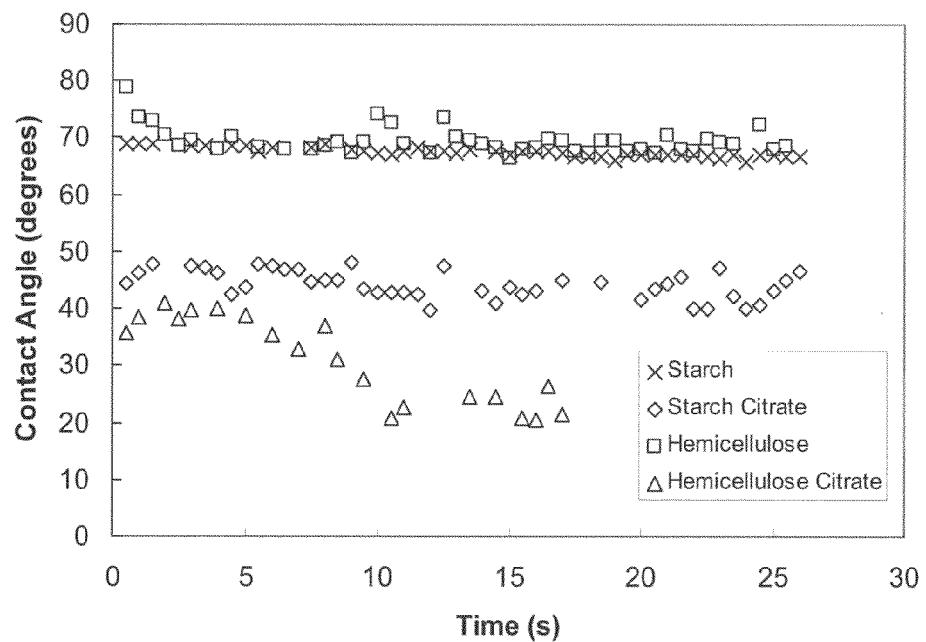
Fig. 3
Fig. 4A                    Fig. 4B

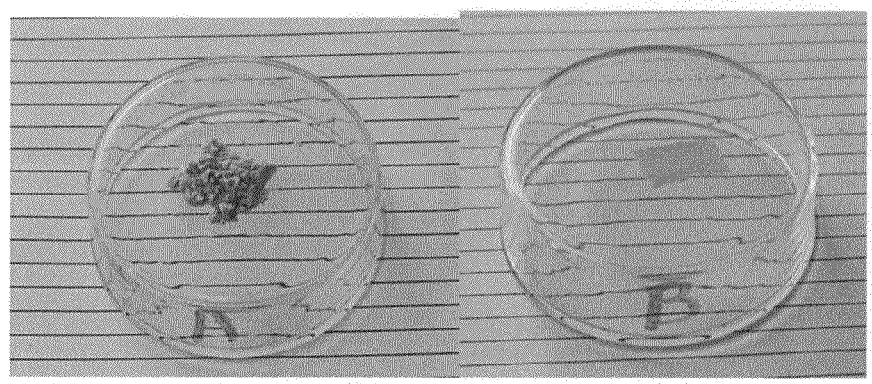
Fig. 5A                    Fig. 5B
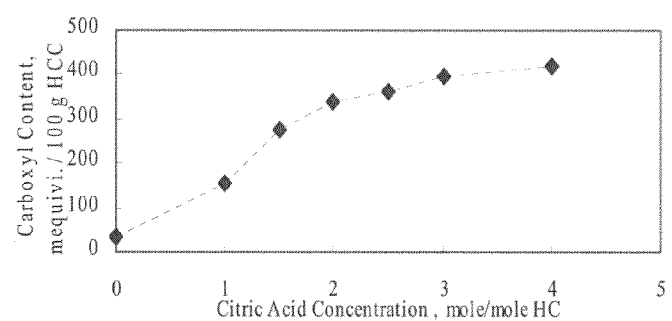
Fig. 6

Fig. 7A
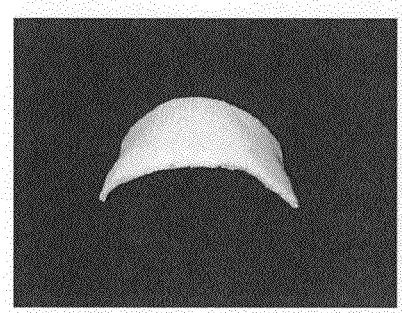
Fig. 7B
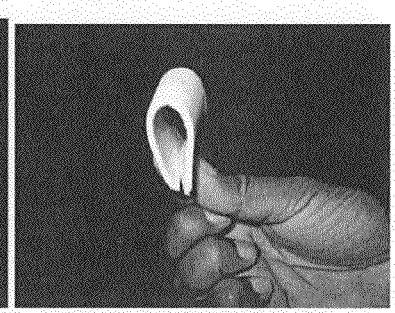
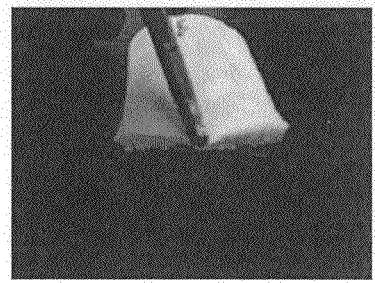
Fig. 7C
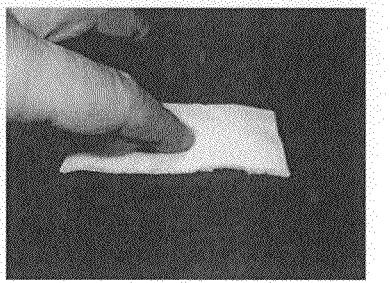
Fig. 7D

A = Chitosan   B = Starch-Chitosan   C = Starch citrate-Chitosan

A = Chitosan   B = Starch-Chitosan   C = Starch citrate-Chitosan

A= Starch citrate-Chitosan Storage Modulus, B= Starch-Chitosan Storage Modulus
C= Starch citrate-Chitosan Loss Modulus, D= Starch-Chitosan Loss Modulus

US 8,975,387 B1

MODIFIED CARBOHYDRATE-CHITOSAN COMPOUNDS, METHODS OF MAKING THE SAME AND METHODS OF USING THE SAME

RELATED APPLICATIONS

This application claims the benefit of U.S. Provisional Patent Application Ser. No. 61/316,311, filed Mar. 22, 2010, titled "MODIFIED CARBOHYDRATE-CHITOSAN COMPOUNDS, METHODS OF MAKING THE SAME AND METHODS OF USING THE SAME", the content of which is incorporated by reference herein in its entirety.

FEDERALLY SPONSORED SUPPORT

This invention was made with government support from the Consortium for Plant Biotechnology, with support originating from the United States Department of Energy under Grant No. DE-FG36-02GO12026. The United States Government may have certain rights in the invention.

TECHNICAL FIELD

The present invention relates generally to modified carbohydrate-chitosan compounds, methods for utilizing modified carbohydrate-chitosan compounds, and methods for producing modified carbohydrate-chitosan compounds. More particularly, the present invention relates to modified carbohydrate-chitosan compounds that include a carbohydrate component, a cross linking agent including acidic groups, and chitosan; or, stated differently, carboxylated carbohydrates cross linked with chitosan.

BACKGROUND

Hemicelluloses are widely abundant polysaccharides in nature, representing about 20-35% of lignocellulosic biomass. Hemicelluloses are estimated to account for one-third of all renewable organic carbon available on earth. R. A. Prade, *Biotechnology and genetic engineering reviews* 1995, 13, 101; E. Sjöström, *Wood Chemistry, Fundamentals and Applications*, Academic Press, Inc., San Diego 1981. Often, hemicelluloses are found as organic wastes or byproducts of renewable forest and agricultural products. A. Ebringerova, Z. Hromadkova, *Biotechnology and genetic engineering reviews,* 1999, 16, 325; C. S. Badal, *Ind. Microbiol. Biotechnol.* 2003, 30, 279. For instance, in the pulp and papermaking process, significant quantities of hemicellulose are solubilized and burned for fuel value. Hemicelluloses have not yet found broad industrial applications similar to cellulose. S. Xaio-Feng, S. Run-Cang, *Science of Food and Agriculture,* 2004, 84(8), 800. The development of new, high-valued products based on hemicelluloses would significantly improve the economics associated with the utilization of lignocellulosic biomass. The chemical composition of hemicelluloses is related to cellulose, but its morphological structure is significantly different. Due to the heterogeneity of their chemical constituents, hemicelluloses in their natural state are generally considered to be non-crystalline and are branched polymers of low molecular weight with a degree of polymerization of 80-200. E. Sjöström, *Wood Chemistry, Fundamentals and Applications*, Academic Press, Inc., San Diego 1981. The most commonly existing sugars that constitute hemicelluloses are D-glucose, D-mannose, D-xylose, D-glucuronic acid, 4-O-methyl-D-glucuronic acid, and D-galacturonic acid. I. Gabrielii, P. Gatenholm, *Applied Polymer Science,* 1998, 69, 1661. The chemical composition and structure of hemicelluloses vary with plant species. The chemical modification of hemicelluloses presents a new avenue for the preparation of materials with special properties that can increase the applications for these biopolymers of abundance. Modifications that can accommodate or overcome issues with molecular weight disparity or variations in chemical composition are especially needed. For years, health care and medical textile industries have been attempting to find new sources of natural biomaterials with performance properties that are comparable with the major natural and synthetic materials currently used such as cotton or acrylics. Highly purified cotton and other natural fibers have significant cost issues associated with them. Synthetic materials are non-renewable and contribute to significant environmental issues such as disposal. Hemicellulose is an abundant biomaterial that has the potential to replace these materials.

Starch is another carbohydrate polymer that is widely abundant and readily available in a number of commercial forms. Starch typically occurs as semi-crystalline granules composed of amylopectin (branched polymer, 4000 glucose units) and amylose (linear polymer, 1000 glucose units). Both amylopectin and amylose are composed of α-1-4-glucosidic units. P. J. Jenkins, A. M. Donald, *Biological Macromolecules,* 1995, 17(6), 315. The ratio of amylose to amylopectin varies significantly and is in part determined by the origin of the starch. A typical corn starch has an amylose content of 75% whereas the amylose percentage for potato and for waxy maize is typically 82% and 0%, respectively. H. F. Zobel, *Starch/Starke,* 1988, 40, 44. The low cost and commercial availability of starch in the market attracts researchers attempting to develop new functional starch derivatives for industrial applications. The industrial applications of starch derivatives depend on the degree of substitution and type of functional groups along the main backbone of the starch polymer, its properties (gelatinization, crystallization, retrogradation, gel formation), and the amylose/amylopectin ratios (which depend on the source of extraction). P. J. Jenkins, A. M. Donald, *Biological Macromolecules,* 1995, 17(6), 315. One disadvantage of using starch relative to hemicellulose is that starch has great demand as a food product, whereas hemicellulose does not.

Chitin is an abundant naturally occurring polysaccharide with annual production very near the levels of cellulose. Chitin consists mainly of β-(1-4)-2-acetamido-2-deoxy-D-glucose units. Despite much recent research into its utilization, its strong intermolecular hydrogen bonding and poor solubility in common organic solvents have so far prevented widespread utilization of chitin. George A. F. Roberts, *Chitin chemistry*, Macmillan, London, 1992, 64. Chitosan is the N-deacetylated form of chitin that is obtained by alkaline treatment of chitin (e.g., treatment with sodium hydroxide (NaOH)) at high temperature. Chitosan is another carbohydrate-based polymer that is very abundant as a byproduct of the fishing industry, is widely available and is of strong research interest. I. M. Helander, E. L. Nurmiaho-Lassila, R. Ahvenainen, J. Rhoades, S. Roller, *International Journal of Food Microbiology,* 2001, 71(2), 235. Chitosan and its derivatives have become useful polysaccharides in the biomedical area because of their biocompatible, biodegradable, and non-toxic properties. K. Y. Lee, W. H. Park, W. S. Ha, *J. Appl. Polym. Sci.,* 1997, 63, 425. The anti-microbial and antifungal activities of chitosan and chitosan derivatives have previously been described. K. F. El-Tahlawy, M. A. El-bendary, A. G. Elhendawy, S. M. Hudson, *Carbohydrate Polymer,* 2005, 60, 421; Sang-Hoon Lim, S. M. Hudson, *Carbohydrate Polymers,* 2004, 56(2), 227. Chitosan has been found to inhibit the growth of a wide variety of bacteria and fungi. Moreover, chitosan has several advantages over other types of disinfectants in that it possesses a higher antibacterial activity, broader spectra of activity, a higher killing rate, and lower toxicity toward mammalian cells.

Several mechanisms were proposed for the antimicrobial activity of chitosan: (1) the polycationic structure of chitosan may interact with the predominantly anionic components (lipopoly-saccharides and proteins of microorganism surface) of cell membranes resulting in changes in the membrane permeability that causes death of the cell by inducing leakage of intracellular components (I. M. Helander, E. L. Nurmiaho-Lassila, R. Ahvenainen, J. Rhoades, S. Roller, *International Journal of Food Microbiology,* 2001, 71(2), 235; M. Vaara, T. Vaara, *Antimicrobiology agents Chemotherapeutant,* 1983, 24, 114; H. Nikaido, *Escherichia coli and Salmonella: cellular and molecular biology*, American Society for Microbiology, Washington, D.C., 1996, 1, 29; S. H. Lim, S. M. Hudsen, *Carbohydrate Research,* 2004, 339, 313); (2) the chitosan on the surface of the cell can form a polymer membrane that prevents nutrients from entering the cell (X. Wang, Y. Du, H. Liu, *Carbohydrate Polymers,* 2004, 56, 21; L. Y. Zheng, J. F. Zhu, K. S. Sun, *Materials Science and Engineering,* 2000, 18, 22; H. Liu, Y. Du, J. Yang, H. Zhu, *Carbohydrate Polymers,* 2004, 55, 291); (3) the chitosan of lower molecular weight enters the cell, binds to DNA and inhibits RNA and protein synthesis (X. F. Liu, Y. L. Guan, D. Z. Yang, Z. Li, K. D. Yao, *J. Appl. Polymer Sci.* 2001, 29, 1324); and (4) since chitosan could adsorb electronegative substances in the cell and flocculate them, chitosan may disturb the physiological activities of the microorganism leading to death of the cells (L. Y. Zheng, J. F. Zhu, *Carbohydrate Polymers,* 2003, 54, 527).

The incorporation of carboxylic acid groups and antimicrobial activity into both hemicelluloses and starches (as well as other biopolymeric carbohydrates) is of interest in order to develop chemical and physical functionality in these materials. Natural polysaccharides with high carboxylic acid content are expected to have superior hydrophilic properties useful in applications such as absorbents.

Recently, new hemicellulose based superabsorbent materials have been synthesized by several scientists. A new hydrogel has been synthesized by graft copolymerization of 2-hydroxyethyl methacrylate (HEMA) or poly(ethylene glycol) dimethacrylate (PEGDMA, a cross linking agent) with oligomeric hydrosoluble hemicellulose modified with well-defined amounts of methacrylic functions. M. S. Lindblad, A.-C. Albertsson, E. Ranucci, *ACS Symposium Series,* 2004, 864 (Hemicelluloses), 347. The grafted copolymer was elastic, soft, and easily swellable in water. The viscoelastic and solution rheological properties of the grafted copolymer were characterized. Also, a comparison of hemicellulose-based hydrogels with pure poly(2-hydroxyethyl methacrylate) hydrogels showed that their behaviors were similar, demonstrating the potential of hemicellulose-based gels to compete with gels derived from petroleum based resources. However, the swelling properties of the hemicellulose/poly(hydroxyethyl methacrylate) were not adequate enough for many applications.

Hemicellulose (xylan) aspen wood has been separated with an alkali extraction method combined with ultrafiltration. I. Gabrielii, P. Gatenholm, W. G. Glasser, R. K. Jain, L. Kenne, *Carbohydrate Polymers,* 2000, 43(4), 367. The hemicellulose was sparingly soluble in cold water but soluble in hot water. Solutions of the hemicellulose did not exhibit good film forming properties. When mixed with chitosan, however, a gel was formed and films could be produced at compositions of 5% chitosan and above in acidic conditions. Ionic complexes between glucuronic acid functionalities of the hemicellulose and amino groups of chitosan were suggested to be responsible for network formation (interpolyelectrolyte complex). The morphologies of these films were examined, and a pure xylan film proved to be crystalline. The crystallinities were found to decrease with an increasing amount of chitosan, and the film of pure chitosan had virtually no crystallinity Films of mixtures of xylan with chitosan displayed slightly higher degrees of crystallinities than would be predicted from the weighted averages of the pure xylan and the pure chitosan films. When immersed in water, films with 5-20% chitosan formed hydrogels, and the degree of swelling of the hydrogels was shown to increase as the films contained more chitosan. Films with more than 20% chitosan dissolved in water. The film and hydrogel forming properties were attributed to crystalline domains of xylan interacting with the chitosan chains, as well as to electrostatic interactions between the acidic groups in the hemicellulose and the amino groups in the chitosan. In this study, the use of unmodified hemicellulose provided only a single, low carboxyl content of the hemicellulose which limited the ionic complexation between the carboxyl groups of hemicellulose and the amino group of chitosan (interpolyelectrolyte complex). This study, in addition to other studies, shows that bio-based materials have strong potential in the production of advanced gel materials.

Accordingly, there is a need for new, high-valued, industrially applicable, and environmentally efficient biomaterials based on hemicellulose, as well as other biopolymeric carbohydrates, that have exceptional performance properties.

SUMMARY

To address the foregoing problems, in whole or in part, and/or other problems that may have been observed by persons skilled in the art, the present disclosure provides compositions, methods, processes, systems, apparatus, instruments, and/or devices, as described by way of example in implementations set forth below.

According to one implementation, a composition of matter includes chitosan and a modified carbohydrate. The modified carbohydrate includes a carbohydrate component and a cross linking agent. The modified carbohydrate has increased carboxyl content as compared to an unmodified counterpart carbohydrate. A carboxyl group of the modified carbohydrate is covalently bonded with an amino group of the chitosan.

In some implementations, the carbohydrate component is selected from the group consisting of hemicellulose and starch.

In some implementations, the cross linking agent is selected from the group consisting of citric acid, succinic anhydride, maleic anhydride and sodium mono chloro acetate.

According to another implementation, a method is provided for making a cross linked modified carbohydrate-chitosan compound. A carbohydrate component is esterified by combining the carbohydrate component with a cross linking agent in an aqueous solution, wherein a mixture including the carbohydrate component and the cross linking agent is formed. The mixture is dehydrated to form a modified carbohydrate. The modified carbohydrate is cross linked with chitosan by reacting the modified carbohydrate with chitosan under aqueous conditions. In some implementations, esterifying the carbohydrate component may include adding a catalyst to the aqueous solution. In some implementations, the catalyst may be selected from the group consisting of sodium hypophosphite, sodium bisulfate and sodium bisulfite. The cross linked modified carbohydrate and chitosan may be freeze dried to form a foam. In some implementations, the foam may be cured by heating the foam at a predetermined temperature for a predetermined time to increase the tensile strength of the foam.

According to another implementation, a method is provided for making a cross linked starch citrate-chitosan compound. An aqueous citric acid solution including citric acid, water and a catalyst is provided. A starch component is reacted with the citric acid solution to provide a starch citrate solution. The starch citrate solution is mixed with a chitosan solution including chitosan, water and a weak acid to produce the cross linked starch citrate-chitosan compound.

According to another implementation, a method is provided for making a cross linked hemicellulose citrate-chitosan compound. An aqueous citric acid solution including citric acid, water and a catalyst is provided. A hemicellulose component is reacted with the citric acid solution to provide a hemicellulose citrate solution. The hemicellulose citrate solution is mixed with a chitosan solution including chitosan, water and a weak acid to produce the cross linked hemicellulose citrate-chitosan compound.

According to another implementation, a water absorption process includes contacting water with a cross linked modified carbohydrate-chitosan compound.

According to another implementation, a salt solution absorption process includes contacting a solution containing salt with a cross linked modified carbohydrate-chitosan compound.

According to another implementation, a metal chelation process includes contacting a solution containing a metal with a cross linked modified carbohydrate-chitosan compound.

According to another implementation, a salt absorption process includes contacting a solution containing salt with a cross linked modified carbohydrate-chitosan compound.

Other compositions, devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1A is an image of a sample of hemicellulose.
FIG. 1B is an image of a sample of hemicellulose citrate.
FIG. 1C is an image of a sample of starch.
FIG. 1D is an image of a sample of starch citrate.
FIG. 3 is a plot of water contact angle as a function of time for starch, starch citrate, hemicellulose and hemicellulose citrate.
FIG. 4A shows a water drop after 0.5 seconds of contact with the surface of a starch citrate tablet.
FIG. 4B shows a water drop after 30 seconds of contact with the surface of a starch citrate tablet.
FIG. 5A is an image of hemicellulose powder before reacting with citric acid.
FIG. 5B is an image of hemicellulose citrate gel film after reacting the hemicellulose powder of FIG. 5A with citric acid, using a material-to-water ratio of 1/0.5 (wt/wt) with a reaction time of three hrs at 100° C. with no catalyst.
FIG. 6 is a plot of the carboxyl content of hemicellulose citrate vs. citric acid concentration in the reaction medium during the reaction of the hemicellulose powder of FIG. 5A with citric acid, using a material-to-water ratio of 1/0.5 (wt/wt) with a reaction time of three hours at 100° C. with no catalyst.
FIG. 7A is an image of unstressed flexible foam material made from hemicellulose citrate-chitosan under the following reaction conditions: a 1:1 ratio of hemicellulose citrate to chitosan, reaction time of three hours, a 1:100 ratio of solid to liquid, pH=3.5 and temperature of 110° C.
FIG. 7B is an image of the foam material of FIG. 7A, showing the foam material being folded.
FIG. 7C is an image of the foam material of FIG. 7A, showing the foam material with a localized impression.
FIG. 7D is an image of the foam material of FIG. 7A, showing the foam material being flattened.

DETAILED DESCRIPTION

Figure 2A:
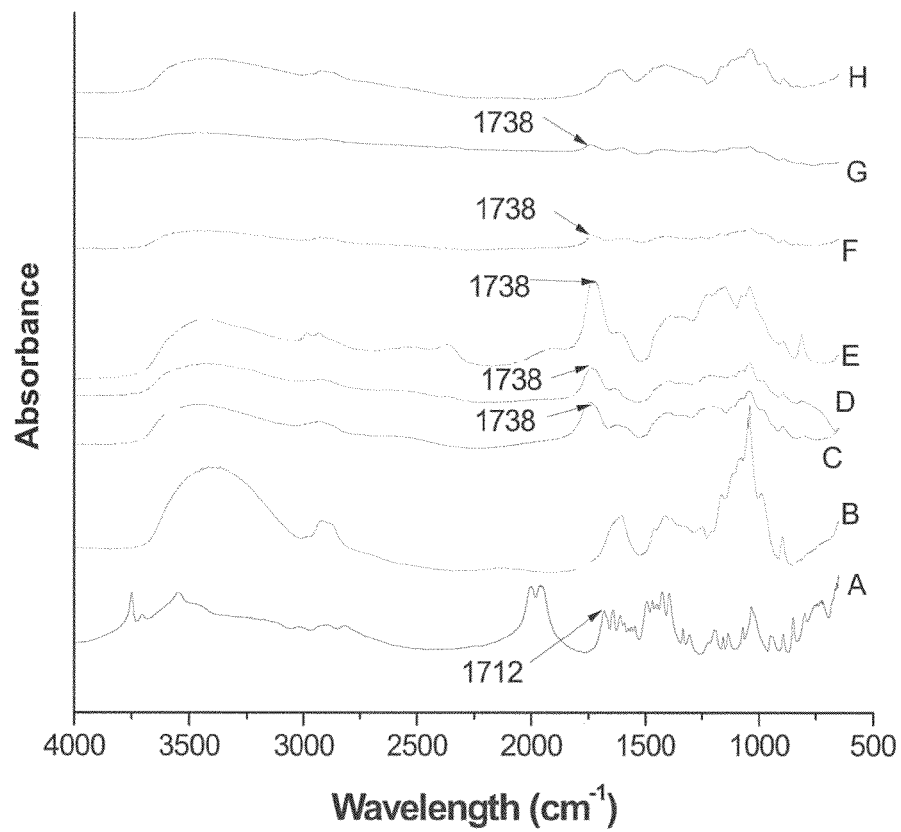
FIG. 2A shows FTIR spectra of citric acid (A), hemicellulose (B), hemicellulose citrate in semi-dry oven (C), hemicellulose citrate+20% sodium hypophosphite in semi-dry oven (D), hemicellulose citrate+20% sodium hypophosphite in acid solution method (E), hemicellulose-succinic anhydride (F), hemicellulose-sodium monochloroacetate (G), and hemicellulose-propylene oxide (H).

The present disclosure describes novel cross linked modified carbohydrate-chitosan compounds, methods of making cross linked modified carbohydrate-chitosan compounds, and methods of using cross linked modified carbohydrate-chitosan compounds.

As used herein, the term "carbohydrate" or "carbohydrate component" refers to a compound containing carbon, hydrogen and oxygen with the ratio of hydrogen to oxygen being about 2:1. Carbohydrates may contain various functional groups, including hydroxyl groups, carboxyl groups, and either aldehyde or ketone groups, for example. Carbohydrates include monsaccharides, oligosaccharides of from two to about ten monosaccharide units, and larger polysaccharides, which can contain hundreds of monosaccharide units. Non-limiting examples of the larger polysaccharides include starch (such as amylase and amylopectin), glycogen, dextran, inulin, cellulose, hemicellulose, arabinoxylan, chitin, beta-glucan, glycosaminoglycans, agar, carrageenan, guar gum, pectin, xanthan gum, glucomannan and the like.

As used herein, the term "modified carbohydrate" refers to a carbohydrate derivative that has a higher acidic content (e.g., carboxyl group content) than the carbohydrate from which the modified carbohydrate is derived (i.e., the unmodified counterpart carbohydrate).

As used herein, the term "chitosan" refers to the N-deacetylated form of chitin that is obtained by alkaline treatment of chitin (e.g., treatment with NaOH) at high temperature. The term "chitosan" also refers to precursors of chitosan (e.g., not fully N-deacetylated), and chemical relatives and derivatives of chitosan.

As used herein, the terms "modifying agent" and "cross linking agent" may be used interchangeably to refer to a chemical compound that is used to introduce cross linking and carboxyl (i.e., acidic) functionality (or increase the carboxyl functionality) in the carbohydrate or carbohydrate component. Reacting the cross linking agent with the carbohydrate produces a modified carbohydrate, and provides for the covalent bonding of a carboxyl group of the modified carbohydrate with an amino group of chitosan. Non-limiting examples of modifying agents include citric acid, succinic anhydride, sodium monochloroacetate, maleic anhydride and the like.

As used herein, the terms "solid:liquid ratio" and "material:liquor ratio" may be interchangeably used to refer to the ratio of solid content to liquid content present during the step of cross linking the modified carbohydrate with chitosan. The "solid" or "material" content present during the cross linking step may be used to refer to the amount of modified carbohydrate and chitosan present during the cross linking step.

The present teachings provide cross linked modified carbohydrate-chitosan compounds. In general, a carboxyl group of a modified carbohydrate may be covalently bonded with an amino group of chitosan. The modified carbohydrate has increased carboxyl content as compared to an unmodified counterpart carbohydrate (i.e., a carbohydrate from which the modified carbohydrate is derived). The modified carbohydrate generally includes a cross linking agent and a carbohydrate component. The carbohydrate component may include, for example, hemicellulose, starch, derivatives thereof, and the like. The cross linking agent may include citric acid, succinic anhydride, sodium monochloroacetate, maleic anhydride, derivatives thereof, and the like. The cross linking agent provides increased acidic group content (e.g., carboxyl group content) to the carbohydrate component, and provides for the chemical bonding of a carboxyl group of the modified carbohydrate with an amino group of chitosan. Non-limiting examples of the modified carbohydrate-chitosan compounds include hemicellulose citrate-chitosan and starch citrate-chitosan, as well as others described below.

As demonstrated below by way of non-limiting examples, modified carbohydrate-chitosan compounds according to the present teachings exhibit excellent water absorption properties. The increased water absorption property of these novel compounds provides for a great number of biomedical and technological applications such as drug delivery systems (C. L. Bell, N. A. Peppas, *J Controlled Release*, 1996, 39, 201), soft contact lenses (E. Brinkman, L. Van der Does, A. Bantjes, *Biomaterials*, 1991, 12(1), 63), immobilization of enzymes (A. B. Moustafa, T. Kahil, A. Faizalla, *J. Appl. Polym. Sci.*

2000, 76(4), 594), and artificial implants (D. F. Williams, *Concise Encyclopedia of Medical and Dental Materials*, Pergamon Press, Oxford, England, 1990). Other practical applications of such materials include the use of the modified carbohydrate-chitosan cross linked compounds as flocculants for treatment of sludge (M. Okazaki, T. Hamada, H. Fujii, A. Mizobe, S. Matsuzawa, *J. Appl. Polym. Sci.*, 1995, 58(12), 2243), release of agrochemicals (E. Karadag, D. Saraydin, Y. Caldiran, O. Guven, *Polymers for Advanced Technologies*, 2000, 11(2), 59), protein absorption and recovery (S. H Gehrke, N. R. Vaid, J. F. McBride, *Biotechnology and Bioengineering*, 1998, 58(4), 416), gas separation (Y. I. Park, K. H. Lee, *J. Appl. Polym. Sci.* 2001, 80(10), 1785) and removal of toxic heavy metal ions (G. Zhang, S. Xie, Y. Guo, F. Lu, *Xi'Van Jiaotong Daxue Xuebao*, 2002, 36(5), 541) and other metals from solution. In some implementations, the modified carbohydrate-chitosan compounds may be used as chelating agents to remove heavy metals (e.g., lead (Pb), mercury (Hg), cadmium (Cd), and the like) from solution, arsenic (As) from solution, and other metals (e.g., copper, calcium, magnesium, silver, boron and the like) from solution. In some implementations, the modified carbohydrate-chitosan compounds may be used to absorb salt ions (e.g., $K^+$, $Cl^-$, $Na^+$, $Cl^-$ and the like) and/or various salt compounds (e.g., KCl, NaCl, and the like) from salt-containing solutions. It will be understood that in the present context, the term "salt" encompasses dissociated salt ions (e.g., $K^+$, $Cl^-$, $Na^+$, $Cl^-$ and the like) as well as salt compounds (e.g., KCl, NaCl, and the like). The modified carbohydrate-chitosan compounds according to the present invention may be used in various water and other fluid absorption applications, such as feminine hygiene products, diapers, and the like. As described below, the modified carbohydrate-chitosan compounds according to the present invention may be freeze dried to produce foam materials for various applications. Other important applications may include wound dressings, health care products such as diapers, bandages, hemostatic materials, disposable towels, animal bedding, disposable food and waste containers, films, bags and containers to hold sensitive materials such as medical devices, foods, pharmaceutical or biohazards.

In one implementation, a method of making a cross linked modified carbohydrate-chitosan compound is provided. The method generally includes an esterification step, wherein a carbohydrate component and a cross linking agent are combined to form a mixture, and the mixture is dehydrated to form the modified carbohydrate (i.e., the carboxylated carbohydrate). The method also generally includes a cross linking step, wherein the modified carbohydrate and a chitosan solution are reacted under aqueous conditions to form the modified carbohydrate-chitosan compound.

In some implementations, citric acid may be utilized as the cross linking agent in the esterification step. A citric acid solution including citric acid, water and a catalyst (e.g. sodium hypophosphite, sodium bisulfate, sodium bisulfite, and the like) may be provided. The citric acid solution may be reacted with a carbohydrate component (such as hemicellulose or starch) to provide a modified carbohydrate (e.g., hemicellulose citrate or starch citrate) in solution. The esterification step provides a modified carbohydrate with increased carboxyl content as compared to an unmodified counterpart carbohydrate. In the cross linking step, the modified carbohydrate solution may be mixed with a chitosan solution generally containing chitosan, water and a weak acid to produce the cross linked modified carbohydrate-chitosan solution (e.g., hemicellulose citrate-chitosan or starch citrate-chitosan). In the cross linking step, a covalent bond is generally formed between a carboxyl group of the modified carbohydrate and an amino group of chitosan. Those of skill in the art will appreciate that various carbohydrates and cross linking agents may be utilized in conjunction with the present method, and various esterification step parameters and/or cross linking step parameters may be utilized in conjunction with the present method, as discussed below.

In some implementations, the esterification step may include the addition of a catalyst, such as sodium hypophosphite, sodium bisulfate, or sodium bisulfite. Other catalysts may also be used in the esterification step.

In some implementations, the method of making a cross linked modified carbohydrate-chitosan compound further includes a freeze drying step, wherein the modified carbohydrate-chitosan is freeze dried to form a foam.

In some implementations, the carbohydrate component may comprise hemicellulose, and the cross linking agent may comprise citric acid.

In some implementations, the cross linking agent is selected from the group consisting of citric acid, sodium monochloroacetate, succinic anhydride, and maleic anhydride.

In some implementations, the carbohydrate component may comprise starch, and the cross linking agent may comprise citric acid.

In some implementations the cross linking step may be carried out at a temperature of about 80° C. to about 120° C.

In some implementations the cross linking step may be carried out at a solid to liquid ratio of at least 1:100.

In some implementations the cross linking step may be carried out at a pH of about 3 to about 6.

In some implementations, the cross linking step may be carried out with a modified carbohydrate to chitosan mass ratio of about 0.4:1 to about 1.2:1.

Modified carbohydrate-chitosan compounds according to the present teachings may be utilized in various applications. For example, modified carbohydrate-chitosan compounds in the form of foams may be utilized as components in diapers or feminine hygiene products. Modified carbohydrate-chitosan compounds and foams thereof may also be used to remove salts and/or metals from solution. Modified carbohydrate-chitosan foams may be used in devices that are used to remove salts and/or metals from solution, for example. As another example, modified carbohydrate-chitosan compounds and foams thereof may be used as components in ion-exchange systems, metal chelation systems, and desalination systems. As yet another example, applications of modified carbohydrate-chitosan compounds according to the present invention may entail the use of modified carbohydrate-chitosan compounds and foams thereof as components in membranes for various separation technologies, or as a component in a filter to capture heavy metals and/or salts from solution. Modified carbohydrate-chitosan compounds and foams thereof according to the present teachings may be used in various water remediation applications.

The following examples are intended to illustrate the invention, and are not intended to limit the scope of the invention.

EXAMPLE 1

In this Example, experimental results associated with the utilization of various modifying agents to incorporate hydrophilic groups into starch and hemicelluloses for improved absorbency are presented. Starch (S) and hemicellulose (HC) were modified separately with four different cross linking agents, including: (1) citric acid (CA); (2) succinic anhydride (SA); (3) sodium monochloroacetate (SMCA), and propylene oxide (PO). The hemicellulose or starch was reacted with CA in the presence or absence of sodium hypophosphite (SHP) as a catalyst and in a water solution or in a high solids content state in an oven. Acid-base titrations, Fourier transform infrared spectroscopy (FTIR), thermal gravimetric analysis (TGA), differential scanning calorimetry (DSC) and gas chromatography (GC) were used to confirm the composition of the reaction products. Reacted starch and hemicellulose both had significantly increased carboxyl content, degree of esterification (DE) and degree of substitution (DS) with CA, SA, and SMCA. Effective reaction conditions were determined for high yield products. The catalyst SHP increased yield significantly and increased the DS marginally. SA, SMCA and PO had high yields. The results of the experiments indicate that high carboxyl content materials can be generated using CA, SA or SMCA and that these materials have enhanced water affinity.

Material

Corn starch, lot # C3J121B, was supplied by Cargill Incorporated, Minneapolis, Minn. The starch comprises approximately 25% amylose and 75% amylopectin per the supplier. The hemicellulose utilized was xylan from birchwood with xylose residues of greater than 90% by high performance anion-exchange chromatography (HPAEC), product number X0502, purchased from Sigma-Aldrich, St Louis, Mo. A xylan structure based on the CAS registry number 9014-63-5 is shown below. For calculation purposes, the molecular formula used was $(C_5H_8O_4)_n$ with an average hydroxyl content per sugar moiety equal to one.

ambient conditions to room temperature for approximately one hour. The reaction mixture was then slowly added into 50 ml of IPA in a glass beaker resting in a water-ice bath. The precipitated solid was collected by filtration on filter paper using a house vacuum and the product was air dried. D. Christian, D. S. Roberta, S. Francesca, S. Alessandro, V. Giuseppe, M. Alfonso, N. Luigi, *Applied Polymer Science*, 2008, 110(4), 2453.

Modification of HC/S with CA in Semi-Dry Condition

Five grams of CA was dissolved in a minimal amount of water (six ml) in a glass beaker. HC or starch (five grams) was combined with the CA solution in a 100 ml glass beaker and manually mixed vigorously with a glass rod. The mixture was placed in a forced air oven to dehydrate at 100° C. for 30 minutes. At this point, all surface moisture was removed and the HC or starch particles were coated with CA. The mixtures were allowed to react in the oven at pre-determined conditions. The reaction conditions for the HC samples were five hours at 115° C. and for the S samples were six hours at 120° C. The times and temperatures for reaction were determined from several trial experiments in which times and temperatures were varied. Reaction products were slurried in water (60 ml) for 30 minutes, adjusted to pH=2 using acetic acid, filtered on filter paper, and washed with water (100 ml). The product was air dried overnight and the filtrate was evaporated to obtain a weight for yield determination. E. Robert, P. Wing, *Starch/Starke*, 1996, 48 (7/8), S 275.

Modification of HC/S with SA

In a 250 ml round bottom flask, two grams of HC or S were added to a 1:1 water/ethanol mixture at a 1:20 ratio of carbo-

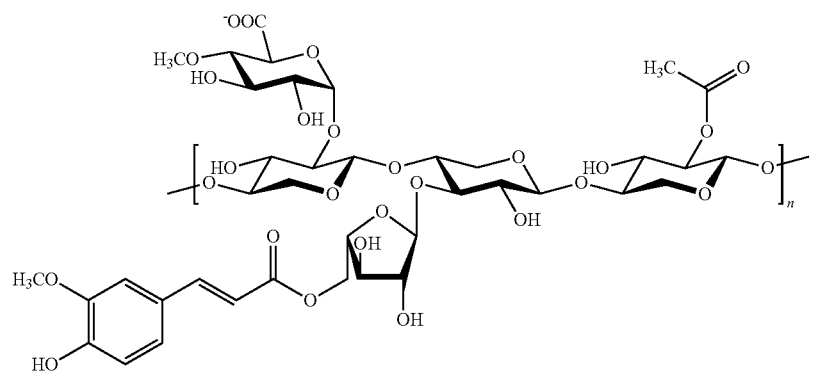

Chemicals of reagent grade utilized were SHP, CAS registry number 123333-67-5; sodium hydroxide, CAS registry number 1310-73-2; SMCA, C. L. number 29, 177-3; PO, CAS registry number 75-56-9 from Sigma-Aldrich, St Louis, Mo.; SA, CAS registry number 452643/1 from Fluka Chemie GmbH, CH-9471, Buchs; CA, CAS registry number 77-92-9; dimethyl sulfoxide (DMSO), L. number 741643; and isopropanol (IPA), L. number 065588 from Fisher Scientific, Fair Lawn, N.J. The Whatman filter paper (quantitative number 4, 110 mm diameter) from Whatman International Ltd, Maidstone, England, was used throughout. Deionized water was used throughout.

Modification of HC/S with CA in Solution

In a 250 ml round bottom flask, three grams of HC or S were treated with 14 grams of CA (in a 14:60 CA (g) to water (ml) solution) in the presence of SHP (20% by weight on CA). The flask was equipped with a reflux condenser and immersed in an oil bath. The reaction mixture was stirred using a magnetic stirrer for three hours at 100° C., followed by cooling in hydrate to liquid. Six grams of SA and four ml of a 15% NaOH solution were also added to the flask. The flask was equipped with a reflux condenser and immersed in an oil bath. The reaction mixture was stirred using a magnetic stirrer for three hours at 100° C. The contents were cooled in ambient conditions to room temperature. The reaction mixture was then slowly added to 200 ml of a water/ethanol mixture (1:1) in a glass beaker resting in a water-ice bath. The precipitated solid was collected by filtration on filter paper, and the product was air dried. F. S. Xaio, R. C. Sun, M. S. Baird, *Carbohydrate Polymers*, 2003, 53(4), 483.

Modification of HC/S with SMCA

Five grams of HC or S was suspended in 150 ml of IPA. A NaOH solution was added (10 ml at 15%) and the mixture vigorously stirred at room temperature for 1 hour. Next, 4.3 grams of SMCA was added and the temperature of the reaction bath was raised to 55° C. over a time period of approximately 10 minutes. The esterification reaction was allowed to continue for 5 hours. The product was filtered on filter paper, suspended in an 80% aqueous methanol bath (about 500 ml), neutralized with glacial acetic acid, and washed with 100 ml water. The product was dried at 60° C. in a forced air oven. K. Petzold, K. Schwikal, T. Heinze, *Carbohydrate Polymers*, 2006, 64(2), 292.

Modification of HC/S with PO

In a reaction flask, 2.5 grams of HC or S was charged with 10 ml of a 15% NaOH solution (pH=12) and stirred at room temperature (around 22° C., below the boiling point of PO, 30° C.) for two hours until the HC or S was dissolved (not visible to the eye). The reaction mixture was then cooled indirectly in an ice water bath and stirred. A quantity of 2.5 ml of PO was added drop wise to the HC or S mixture. The mixture was stirred at ambient temperature for 12 hours. The reaction mixture was cooled indirectly with ice water again, and an additional 2.5 ml of PO was added drop wise (about 5 minutes). The flask was allowed to slowly warm to room temperature with stirring (magnetic stir bar) for an additional 12 hr. The reaction mixture was then precipitated into 75 ml of acetone with stirring. A suspension formed and was allowed to settle and the supernatant decanted. Two successive washing and decanting steps with 13 ml quantities of fresh acetone were then performed. The precipitate was collected by filtration on filter paper and dried in an air oven at 40° C. for 12 hours. K. J. Rajesh, S. Markku, G. G. Wolfgang, *Cellulose*, 2001 7(4), 319.

Determination of Carboxyl Content

Using an acid-base titration, a known amount of synthesized product dissolved in excess 0.1N NaOH (pH=12.5) was allowed to react with the sample as an ester for one hour. The remaining excess amount of NaOH was determined by titration with 0.1N HCl using phenolphthalein as an indicator and the carboxyl content in milliequivalents of acidity per 100 grams calculated as:

$$\text{Carboxyl Content} = \frac{(V_b - V_a) * N * 100}{W}$$

$N$ = Normality of HCl (eq/liter)

$V_b$ = Volume of HCl without sample (ml)

$V_a$ = Volume of HCl without in presence of sample (ml)

$W$ = Weight of Sample (g)

Determination of DE and DS

The synthesized product was dissolved in DMSO in a conical flask for 12 hours, and then excess NaOH was added to the solution to saponify the ester for two hours. The excess NaOH was determined by titration with calibrated HCl to determine the DE and DS:

$$\text{Degree of Esterification} = (\%) = \frac{6.005(V_b - V_a) * F * 100}{W}$$

$F$ = Normality of HC eq/liter $V_b$ = Volume of HCl without sample, ml $V_a$ = Volume of HCl in presence of sample, ml $$\text{Degree of Substitution (DS)} = \frac{162 \times A\%}{100M - (M-1)A\%}$$

$A\%$ = Degree of Esterification $M$ = Molecular weight of cross linking agent (grams/mole)

FTIR Characterization

The FTIR spectra were recorded on a NEXUS 670 FTIR spectrophotometer using a KBr disc containing 10% finely ground samples. All the spectra were obtained by accumulation of 256 scans, with resolution of 4 cm$^{-1}$, at 400-4000 cm$^{-1}$.

TGA

The thermogravimetric analyzer used in this study was a TGA Q500 (TA Inc, New Castle Del.). The sample sizes ranged from 2-11 mg, depending on the density of the material. A nitrogen atmosphere was used. The temperature range and heating rate were 30-600° C. and 10° C./min, followed by isothermal heating at 600° C. for 2 minutes. A. Diana, G. Miguel, O. Roberto, V. T. Humberto, D. S. S. José, S. Keiko, *Carbohydrate Polymers*, 2009, 77(3), 536-543.

DSC

Hermetically sealed pans were used in a DSC (Q100 TA Inc, New Castle Del.) to analyze the thermal characteristics of the samples. The scanning temperature range and the heating rate were 30-200° C. and 5° C./minute with isothermal heating at 200° C. for 2 minutes, followed by cooling rapidly to room temperature. An empty pan was used as a reference. S. Rui, Z. Zizheng, L. Quanyong, H. Yanming, Z. Liqun, C. Dafu, T. Wei, *Carbohydrate Polymers*, 2007, 69(4), 748.

GC

Identification of the esterifying agent was carried out with a GC (Hewlett-Packard 6890, Serial no. US 94206197, USA). The sample was dissolved in a DMSO and acetone mixture (1:10) and then silylated with trimethylsilylate at a 1:1 ratio. The column was temperature-programmed from 50-250° C. (5° C./minute) and the retention time was 34 minutes. The injector and detector temperatures were 220° C. and 250° C., respectively. The carrier gas helium was fixed at 22 psi. C. Vaca-Garcia, S. Thiebaud, M. E. Borredon, G. Gozzelino, *American Oil Chemists' Society*, 1998, 75(2), 315.

Contact Angle

Dynamic contact angle measurements were performed with a Phoenix 300 Contact Angle Analyzer (Seo Co., Ltd., Korea) on the hemicellulose and starch and the citrates produced from the semi-dry oven method in the presence of SHP. Deionized water was used as the probe fluid on cast films formed on glass petri dishes, which were then air dried. The time interval for image acquisition was 0.5 seconds and data was collected for about 30 seconds.

Results of Modification Reactions of S and HC

The reaction paths that are expected for the four different chemical modifying agents are shown below. All of the reactants act as cross linkers for the carbohydrates. The CA, SA and SMCA increase the carboxyl content of the carbohydrates. The PO does not increase the carboxyl content, but increases the hydroxyl group content.

Esterification of starch with sodium monochloroacetate

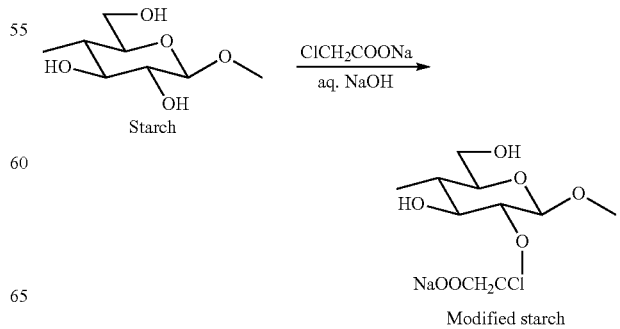

Esterification of starch with propylene oxide

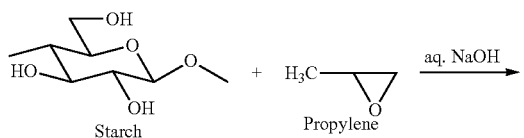
Starch      Propylene Oxide

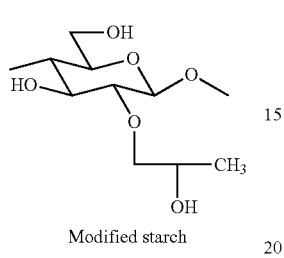
Modified starch

Esterification of starch with succinic anhydride

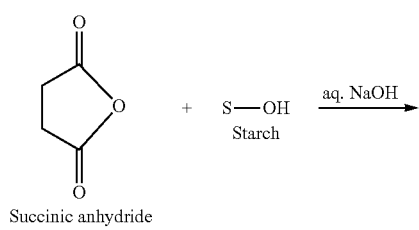
Succinic anhydride

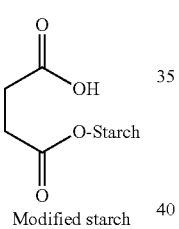
Modified starch

Esterification of starch with citric acid
I) Formation of citric acid anhydride

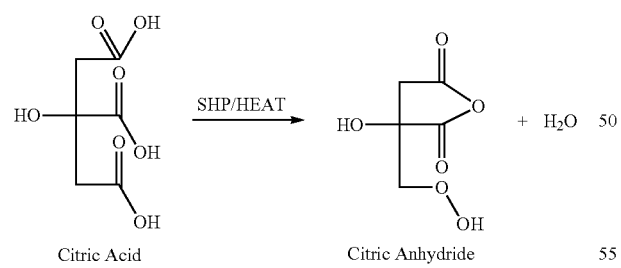
Citric Acid      Citric Anhydride

II) Esterification of Starch

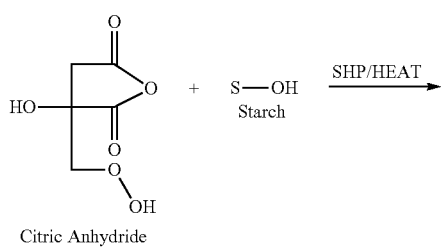
Citric Anhydride

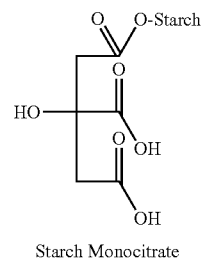
Starch Monocitrate

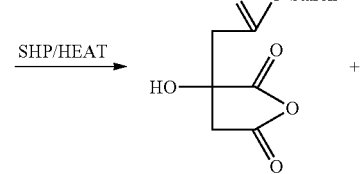

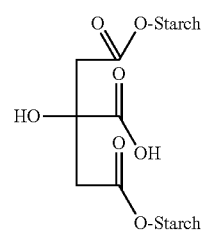
Modified starch

HC, hemicellulose citrate (HCC), S and starch citrate (SC) are shown in FIGS. 1A-1D, respectively. As illustrated in FIGS. 1A-1D, the reaction with CA darkens the material. As shown in Table 1 below, the percent yield of both the HCC and SC using the semi-dry oven method was significantly higher than the percent yield from the CA solution method. This may be explained in that in the semi-dry oven method the CA is not diluted, readily produces citric anhydride and is in close proximity to the S or HC. For both HC and S, the use of the catalyst SHP further increases the yield. The reaction yields of the reactions of SA, SMCA and PO with both HC and S were high. In the case of SMCA, for both HC and S, yields of over 100% relative to the starting carbohydrate were observed.

Table 1: Results of reactions of S and HC with various cross linking agents (ND—not detectable).

TABLE 1

Results of reactions of S and HC with various cross linking agents (ND—not detectable).

| Sample | Cross linking agent | Catalyst (wt %) | Reaction Process | Color | Yield (%) | Carboxyl content (mequ/100) | Degree of esterification (%) | Degree of substitution |
|---|---|---|---|---|---|---|---|---|
| HC | — | — | | Light Tan | 00 | 324 | 00 | 00 |
| | CA | SHP | Solution | Brown | 10 | 729 | 42.3 | 0.55 |
| | CA | — | Semi-dry Oven | Brown | 40 | 722 | 39.3 | 0.49 |
| | CA | SHP | Semi-dry Oven | Brown | 50 | 742 | 42.6 | 0.56 |
| | SA | NaOH | Solution | Brown | 100 | 709 | 34.8 | 0.70 |
| | SMCA | NaOH | Solution | Light Brown | 110 | 484 | 17.0 | 0.23 |
| | PO | NaOH | Solution | Dark Brown | 100 | 352 | 3.2 | 0.08 |
| S | — | — | | White | | ND | ND | ND |
| | CA | SHP | Solution | Golden Yellow | 10 | 448 | 46.6 | 0.8 |
| | CA | — | Semi-dry Oven | Golden Yellow | 42 | 437 | 43.7 | 0.72 |
| | CA | SHP | Semi-dry Oven | Golden Yellow | 76 | 473 | 46.3 | 0.80 |
| | SA | NaOH | Solution | White | 80 | 466 | 37.0 | 0.95 |
| | SMCA | NaOH | Solution | White | 120 | 180 | 20.4 | 0.36 |
| | PO | NaOH | Solution | Dull White | 80 | 00 | 4.4 | 0.13 |

The carboxyl content was increased for the HC from 324 mequ/100 gram to a maximum of 742 mequ/100 gram for CA with SHP in the semi-dry oven method. For S, the carboxyl content was raised from zero to a maximum of 473 mequ/100 gram, also for the CA with SHP in the semi dry oven method. As expected, the PO did not increase the carboxyl content of the carbohydrates.

To further investigate the partial esterification, the DS and DE were determined by titration. For this study, the monomer formula weight and number of hydroxyls' per monomer unit were assumed to be 162 and 3, respectively, for 5 and 132 and 1, respectively, for HC. The DE is the percentage of the reacted hydroxyl groups relative to the total initial hydroxyl groups. DS is expressed as the average number of moles of substituent per anhydroglucose (repeat) unit. The use of SHP as a catalyst increased the DE and DS as well as the yield for the semi-dry oven method for both HC and S. The DE and DS of HC and S with PO was much lower than those formed with other cross linking agents, as shown in Table 1. The DS of HC or S with SA was significantly higher than PO and SMCA, but it was comparable with CA.

Results of FTIR Analysis

The FTIR spectra of CA (A), HC (B), HCC in semi-dry oven (C), HCC+20% SHP in oven (D), HCC+20% SHP in acid solution method (E), HC-SA (F), HC-SMCA (G) and HC—PO (H) are shown in FIG. 2A. Analysis of the FTIR data for HC (B) showed an absorption band in the 1200-1000 $cm^{-1}$ region typical for HC. F. Xu, X. J. Sun, Z. C. Geng, C. F. Liu, J. L. Ren, R. C. Sun, P. Fowler, M. S. Baird, *Carbohydrate Polymers,* 2007, 67(1), 56. This region is dominated by ring vibrations overlapped with stretching vibrations of (C—OH) side groups and the (C—O—C) glycosidic bond vibration. X. Xueju, L. Qiang, W. C. Steve, *Food Research International,* 2006, 39, 332. A strong broad peak due to hydrogen-bonded hydroxyls appears at 3414 $cm^{-1}$.

In the CA spectrum (A), it is possible to observe a C=O band centered at 1712 $cm^{-1}$ due to carboxylic acid. D. Christian, D. S. Roberta, S. Francesca, S. Alessandro, V. Giuseppe, M. Alfonso, M., N. Luigi, *Applied Polymer Science,* 2008, 110(4), 2453. When HC is reacted with CA (C, D, E), SA (F), and SMCA (G), a peak appears at around 1738 $cm^{-1}$, attributable to the characteristic stretching band of carbonyl groups at lower frequencies related to anhydride formation, an intermediate reaction necessary for CA reaction with HC hydroxyl groups. Id. Also, the peak at 3414 $cm^{-1}$ decreases qualitatively, indicating the conversion of hydroxyl to esters. For HC—PO(H), the peak at 1738 $cm^{-1}$ is not observed, as expected, whereas the peak at 3414 $cm^{-1}$ remains qualitatively.

Figure 2B:
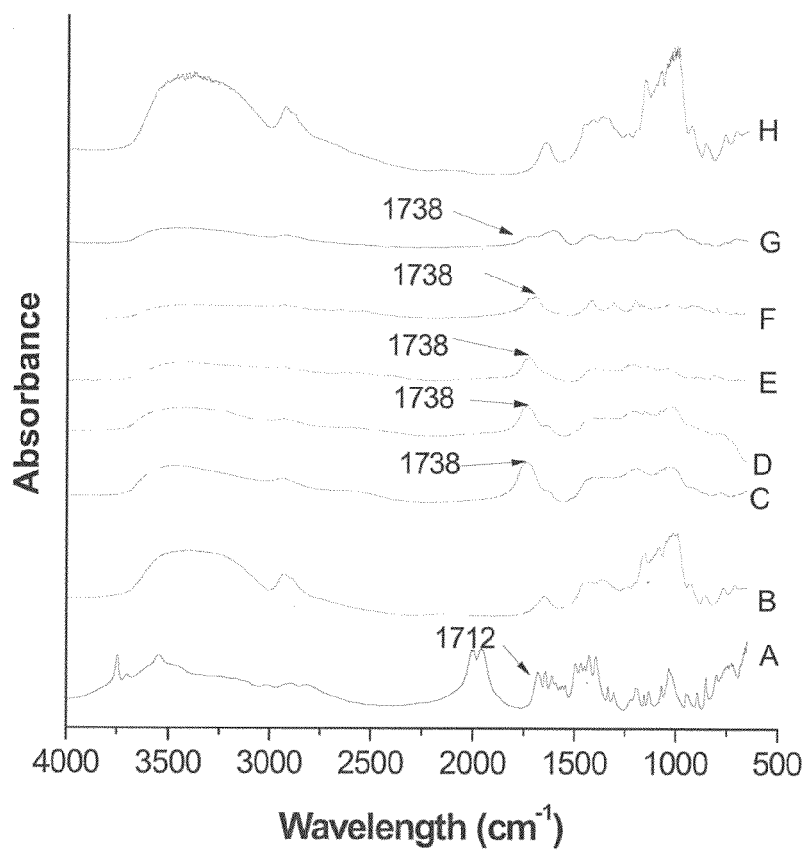
FIG. 2B shows FTIR spectra of citric acid (A), starch (B), starch citrate in semi-dry oven (C), starch citrate+20% sodium hypophosphite in semi-dry oven (D), starch citrate+20% sodium hyphophosphite in acid solution method (E), starch-succinic anhydride (F), starch-sodium monochloroacetate (G), and starch-propylene oxide (H).

FTIR spectra of S (B), SC in semi-dry oven (C), SC+20% SHP in semi-dry oven (D), SC+20% SHP in acid solution method (E), S-SA (F), S-SMCA (G), and S—PO(H) appear in FIG. 2B. For S (B) a prominent peak at 3414 $cm^{-1}$ is apparent due to the hydroxyl groups and there is no peak at 1712 $cm^{-1}$, reflecting that there are no carbonyl groups, as expected in S. When S is reacted with CA (C, D, E), SA (F), and SMCA (G), a peak appears at around 1738 $cm^{-1}$, attributable to the carbonyl group. Also, the peak at 3414 $cm^{-1}$ decreases qualitatively, indicating the conversion of hydroxyl to esters. For the S—PO(H), the peak at 1738 $cm^{-1}$ is not observed, as expected, whereas the peak at 3414 $cm^{-1}$ is prominent. These results confirm the measurements in Table 1 and indicate that both S and HC are reacted in a similar way, as expected.

Results of TGA

The thermogravimetric behavior of HC and S reacted with CA, SA, SMCA and PO was evaluated with a 10° C./minute heating rate under nitrogen. The results of the thermogravimetric analysis are shown in Table 2 below. For several samples a weight loss below and around 100° C. was attributed to water evaporation. However, the weight loss above 100° C. was caused by the thermal decomposition of the HC and S based materials. CA had a single sharp decomposition peak at 191° C. HC had a single weight loss peak at 286° C., whereas for all modified HC materials, a significant decrease in maximum weight loss temperature was observed. Significantly higher residual mass was observed after heating to 600° C. The increased residual mass after heating to 600° C. for the modified HC products is in agreement with the existence of cross linking of the carbohydrate materials. Similar results were observed for S, as shown in Table 2.

Table 2: Results of thermal analysis of S and HC derivatives

TABLE 2

Results of thermal analysis of S and HC derivatives

| Sample | TGA maximum (DTG) degradation temp. (° C.) | Residual char at 600° C., (%) | DSC melting point (° C.) |
|---|---|---|---|
| CA | 191.4 | 6.5 | 158.5 |
| HC | 286.8 | 21.9 | 192.3 |
| HCC in semi-dry oven | 187.1 | 30.7 | 182.1 |
| HCC + 20% SHP in semi-dry oven | 202.3 | 32.5 | 188.1 |
| HCC + 20% SHP in acid solution method | 167.1 | 37.8 | 145.9 |
| HC-SA | 221.3 | 32.7 | 179.6 |
| HC-SMCA | 228.9 | 29.4 | 140.5 |
| HC-PO | 268.8 | 30.5 | 165.2 |
| S | 315.3 | 12.47 | 167.2 |
| SC in semi-dry oven | 258.3 | 24.9 | 157.8 |
| SC + 20% SHP in semi-dry oven | 227.1 | 30.5 | 140.80 |
| SC + 20% SHP in acid solution method | 235.5 | 31.0 | 144.4 |
| S-SA | 227.3 | 32.1 | 149.3 |
| S-SMCA | 298.2 | 39.0 | — |
| S-PO | 287.8 | 23.8 | 129.5 |

The behavior in the DSC of the HC and S reacted with CA, SA, SMCA and PO was evaluated with a 5° C./minute heating rate up to 200° C. under nitrogen. The results of the DSC analysis are also shown in Table 2. CA displays a very sharp melting point at 158.5° C. For untreated HC and S an endothermic peak was observed at 192.3 and 167.2° C., respectively. These peaks are tentatively designated as melting peaks as the thermogravimetric analysis showed no weight loss in this temperature range. The melting points were all decreased for the reaction products. The decrease in the melting point may be from the changes in chemical composition especially with regards to hydrogen bonding and plasticization as well as the interference of molecular organization due to cross linking.

Results of GC

GC is suitable for the analysis of the complex trimethylsilylated citrate. CA was treated with trimethylsilylate and a prominent peak was observed at a retention time centered at 28.62 minutes. To confirm that the CA was incorporated into the S, the SC product from the semi-dry oven method in the presence of SHP was treated with DMSO to cleave the CA and then silylated with trimethylsilylate. This produced a prominent peak observed at a retention time centered at 28.42 minutes, similar to the retention time for CA. Similar results were determined for HCC from the semi-dry oven method in the presence of SHP. These results may be interpreted to mean that the CA was incorporated into the carbohydrate as expected.

Contact Angle Results

It is expected that the citrate materials would display increased water affinity and absorption relative to the unmodified materials. The contact angles with water at 0.5 seconds on samples that formed films were determined to be 78° for HC, 35° for HCC, 69° for 5 and 43° for SC, as can be seen in FIG. 3. The standard deviation of the measurements was significant, attributed to difficulties in preparing flat film surfaces when the films shrunk upon drying. The significant decreases of the contact angle for modified materials relative to the unmodified carbohydrates indicate significant increases in the wettability of the modified materials. The other materials would not form films and for this reason tablets (1 cm diameter) were formed under 10 tons of pressure and contact angles measured, again significantly lower than the unmodified S and HC. In several cases, the carbohydrate matrix would swell up and encompass the water droplet in a rapid manner, as shown in FIGS. 4A and 4B, which show a water drop after 0.5 seconds and 30 seconds, respectively, of contact with the surface of a SC tablet. These materials also had high variability in measured contact angles but still had significantly decreased water contact angle, indicating increased hydrophilicity. Table 3 below summarizes the dynamic contact angle measurement results.

Table 3: Dynamic contact angle (in degrees) of S, SC, HC and HCC. Where an asterisk (*) is present, the contact angle could not be measured since the matrix material swelled upward to encompass the fluid, as shown in FIGS. 4A and 4B.

TABLE 3

Dynamic contact angle (in degrees) of S, SC, HC and HCC.

| Material | Contact Angle (0.5 s) | Standard Deviation | Contact Angle (20 sec) | Standard Deviation |
|---|---|---|---|---|
| S | 83 | 12 | 62 | 6 |
| SC | 43 | 7 | 38 | 9 |
| S-SA | 43 | 14 | * | * |
| S-SMCA | 44 | 18 | * | * |
| S-PO | 45 | 23 | * | * |
| HC | 69 | 9 | 55 | 11 |
| HCC | 26 | 14 | 25 | 4 |
| HC-SA | 51 | 12 | 38 | 12 |
| HC-SMCA | 40 | 16 | 30 | 9 |
| HC-PO | 43 | 6 | 31 | 2 |

Where an asterisk (*) is present, the contact angle could not be measured since the matrix material swelled upward to encompass the fluid, as shown in FIGS. 4A and 4B.

Conclusions

Four chemical modifying agents, CA, SA, SMCA, and PO were used to modify S and HC. Effective reaction conditions were determined. Qualitatively, the S and HC reacted in a similar manner. The product yield for a reaction utilizing CA in the semi-dry oven method was significantly more effective than a solution bath method. The carboxyl group content, DE, and DS of CA with S or HC were significantly increased relative to the unmodified materials. The catalyst SHP increased yield significantly and increased the DS marginally. SA, SMCA and PO had very high yields. The results indicate that high carboxyl content materials can be generated using CA, SA or SMCA and materials with increased water affinity produced.

EXAMPLE 2

In this Example, in order to investigate experimentally whether CA could be introduced in a controlled manner to HC to produce different and high carboxyl contents, experiments were performed. The esterification of HC by CA can introduce high concentrations of carboxylic acid groups that serve to increase swellability and to increase the potential for interactions between the modified cellulose and substances such as chitosan (as will be described in greater detail below) to improve gel properties.

The esterification reaction was carried out using a material-to-water ratio of 1:0.5 (wt/wt) with a reaction time of three hours at 100° C. with no catalyst. The extent of esterification expressed as carboxyl content on the HCC was measured via a simple acid-base titration. The HC powder and HCC film are shown in FIGS. 5A and 5B, respectively.

Increases in the CA concentration in the reaction medium was accompanied by an increase in the carboxyl content of the HCC (expressed as mequiv. carboxyl/100 gram of HCC), as can be seen in FIG. 6. The carboxyl content of the unmodified HC is 32 mequivalent/100 g HC. Esterification of HC with CA raises the carboxyl content to approximately 400 mequivalent/100 g HCC. These results demonstrate that the carboxyl content in the HCC can be controlled in a simple manner, thus providing an effective tool for reproducibly altering the chemical composition of gels and developing desired composition-property relationships.

EXAMPLE 3

In the present Example, experimental results are presented associated with the synthesis of HCC in the presence of SHP in a semi-dry method followed by cross linking with chitosan in an aqueous medium to produce absorbent foams. Cross linking reaction conditions affected the water absorbency, weight loss in water, and strength of the cross linked product.

Material

The HC utilized was xylan from birchwood with xylose residues of greater than 90% by HPAE, product number X0502, purchased from Sigma-Aldrich, St Louis, Mo. A structure based on the CAS registry number 9014-63-5 is shown above in Example 1. For calculation purposes the molecular formula used was ($C_5H_8O_4$), with an average hydroxyl content per sugar moiety equal to one. The chitosan (Medium molecular weight, degree of deacetylation 75-85%) CAS registry number 9012-76-4 was purchased from Sigma-Aldrich, St Louis, Mo. Chemicals of reagent grade utilized were SHP, CAS registry number 123333-67-5; CA, CAS registry number 77-92-9; and sodium chloride, acetic acid, and sodium acetate from Fisher Scientific, Fair Lawn, N.J. Whatman filter paper (quantitative number 4, 110 mm diameter) from Whatman International Ltd, Maidstone, England and deionized water were used throughout. A superabsorbent material (particle size 0.8-1 mm, Small Polymer) based on poly acrylic acid (Watersorb, Fayetteville, Ark.) and commercial cellulose foam Spontex (Mapa Spontex Inc. Columbia, Tenn.) were also used as controls. The sponge composition was 48% pulp, 28% magnesium chloride and 24% cellulose fiber.

Synthesis of HC Derivative with CA in Semi-Dry Oven

The esterification of HC with CA reaction scheme is shown below:

Esterification of Hemicellulose with citric acid

I) Formation of citric acid anhydride

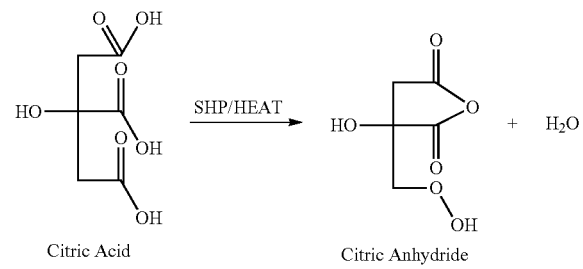

Citric Acid      Citric Anhydride

II) Esterification of Hemicelluloses

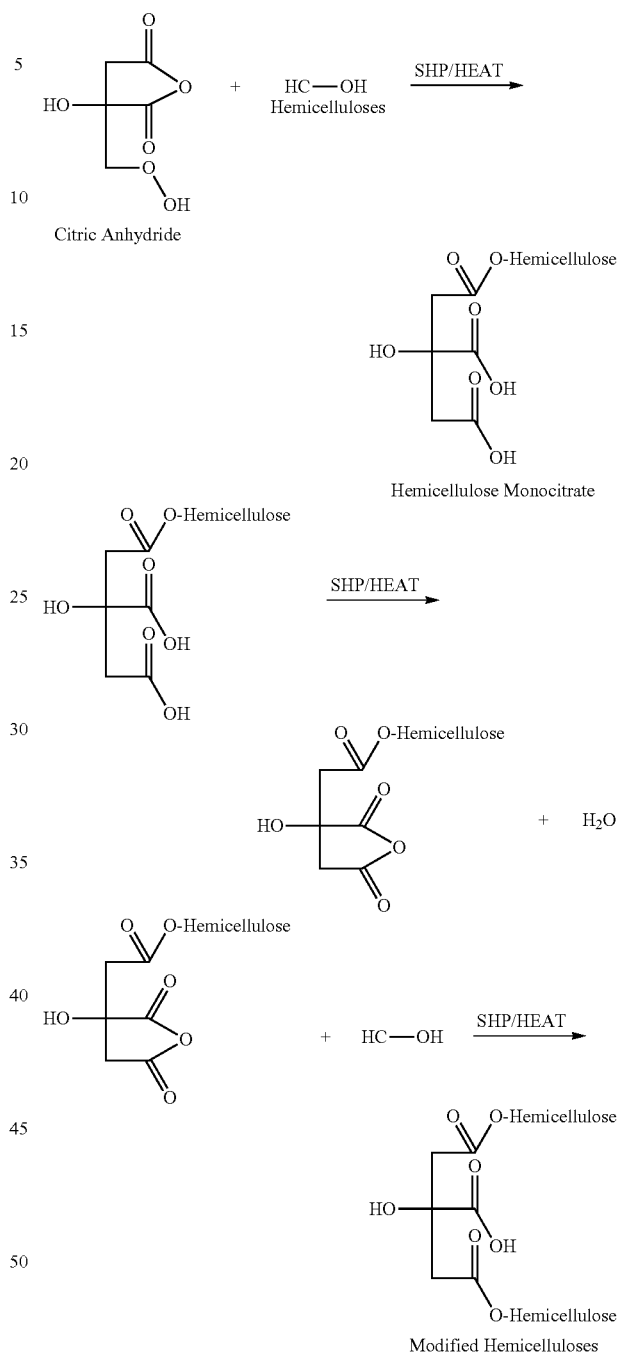

Modified Hemicelluloses

CA (5 g) and SHP (1 g) was dissolved in a minimal amount of water (6 ml) in a beaker. HC (5 g air dried) was combined with the CA solution in a 100 ml glass beaker and mixed vigorously with a glass rod. The mixture was placed in a forced air oven to dehydrate at 100° C. for 30 min. At this point, all surface moisture was removed and the HC particles were coated with CA. The oven temperature was increased to 115° C. (ramp took about 5 minutes) and the material was allowed to react for 5 hours. The times and temperatures for reaction were determined from several previous trial experiments in which times and temperatures were varied. Reaction products were slurried in water (60 ml) for 30 min, adjusted to pH=2 using acetic acid, filtered on filter paper, and washed with water (100 ml). The product was air dried overnight, and the material weighed to determine yield. Id.

Cross Linking Reaction

The cross linking scheme of HCC with chitosan is shown below:

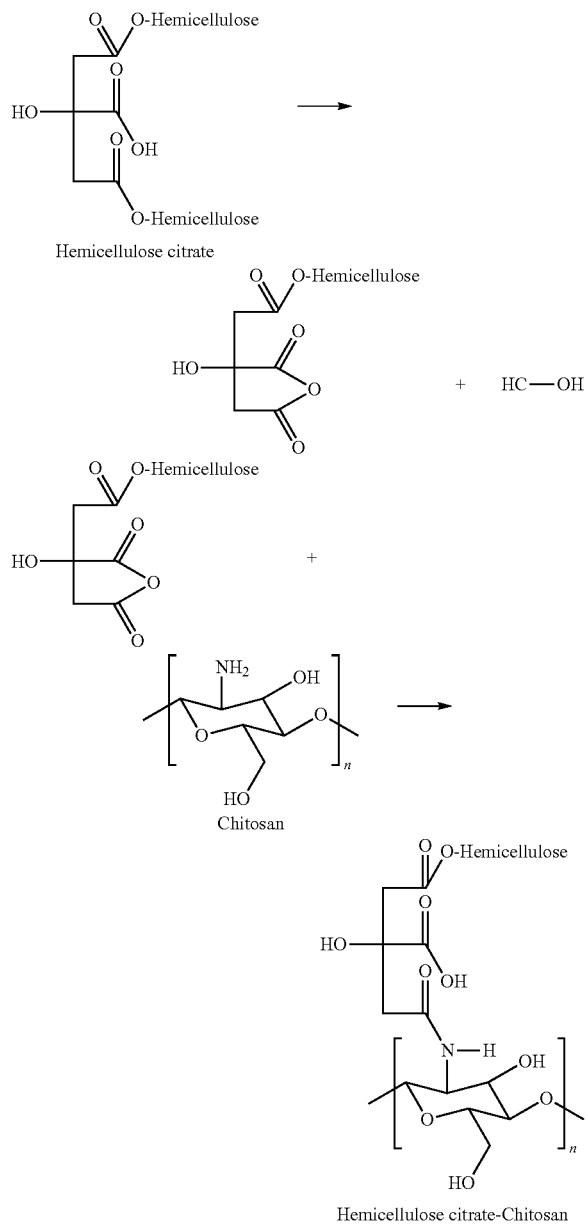

A chitosan solution was prepared by adding 1 gram of chitosan to a mixture of 99 ml of water and 1 ml of glacial acetic acid. The chitosan solution was added to 100 ml of 1% HCC solution in a 500 ml round bottom flask. The pH was then adjusted to 3.5 with sodium acetate. The reaction mixture was stirred using a magnetic stirrer at 110° C. for 3 hours, followed by ambient cooling to room temperature (for approximately one hour) and then the product was freeze dried to create HCC-citrate (HCC—C) foam.

Decantation Method for Determining Water Absorption

A sample of HCC—C foam of around 0.1 grams was weighed (to 0.1 mg), placed in a glass Petri dish of known weight and soaked in 50 ml of distilled water for 0.5, 1 or 48 hours. The water was carefully removed with a 25 ml pipette. The dish and sample were weighed and placed in an oven at 105° C. for two hours. After cooling in a desiccator, the dish and sample were again weighed to determine water absorption and weight loss. Absorption and weight loss with an aqueous NaCl solution (concentration: 0.9%) was investigated similarly. For some samples, the dimensions of the swollen samples were measured using a digital slide caliper. Foams were rectangular in shape and the superabsorbent was assumed to be spherical when dry and disk shaped when wet for volumetric calculations.

Equilibrium Swelling Method for Determining Water Absorption

The equilibrium swelling was determined by a gravimetric method. A pre-weighed wet tea bag of size 200 by 100 mm was used to hold the sample. The sample was immersed into water in a Petri dish at room temperature for a predetermined time, either 0.5, 1 or 48 hours. The sample was then poured into a pre-weighed wet tea bag. The excess water was allowed to drip off the sample due to gravity. The weight of the tea bag and sample was then measured ($X_a$), and the equilibrium swelling (ES) was calculated according to the following formula:

$$ES = \frac{X_a - Y_b - Z_p}{Z_p}$$

$Y_b$ = Weight of wet tea-bag $Z_p$ = Weight of dry sample

Absorption and weight loss with an aqueous NaCl solution (concentration: 0.9%) was investigated similarly.

Vacuum Filtration Method for Determining Water Absorption

Approximately 0.1 g of each sample was weighed and placed in a glass Petri dish. The sample was soaked in 50 ml distilled water for a predetermined time, either 0.5, 1 or 48 hours. A dry Whatman #4 quantitative filter paper circle was placed into a Buchner funnel attached to house vacuum. The contents of the dish were poured onto the filter paper. The dish was rinsed with about 15 ml of additional deionized water and this water was also poured into the funnel Once the water was removed, the sample was lifted off the filter paper and then weighed to determine water absorption per gram of sample. Absorption and weight loss with an aqueous NaCl solution (concentration: 0.9%) was investigated similarly.

Liquid Absorption Under Load Method for Determining Water Absorption

Pre-weighed absorbent samples (0.05 grams) were equilibrated in saline solutions (0.9% NaCl by weight) for one hour. The material was then removed from the solution and placed in the middle of six research grade blotter paper sheets and a weight of 6810 grams applied over an area of 19.6 cm² for 20 minutes. This equates to a pressure of 0.337 kPa gauge (4.90 psig). Some of the water is transferred to the blotter paper. The sample was then removed from the blotter paper and weighed. The saline solution absorbed/sample weight (% wt/wt) was calculated.

FTIR Characterization

The FTIR spectra were recorded on a NEXUS 670 FTIR spectrophotometer using a KBr disc containing 10% finely ground samples. All the spectra were obtained by accumulation of 256 scans, with resolution of 4 cm$^{-1}$, at 400-4000 cm$^{-1}$. Id.

TGA

Thermogravimetric behavior was studied using a TGA Q500 (TA Inc, New Castle Del.) under nitrogen from 30-600° C. at a temperature ramp of 10° C./min followed by isothermal heating at 600° C. for 2 minutes. The differential of the weight loss (differential Thermogram (DTG)) was observed and the maximum in the DTG was reported. A. Diana, G. Miguel, O. Roberto, V. T. Humberto, D. S. S. José, S. Keiko, *Carbohydrate Polymers,* 2009, 77(3), 536.

DSC

A DSC (DSCQ100 (TA Inc, New Castle Del.)) was used with a Hermetic pan (T 090127). Samples were subjected to a 5° C./min temperature ramp from 30-200° C. followed by isothermal heating at 200° C. for 2 min. An empty pan was used as a reference. S. Rui, Z. Zizheng, L. Quanyong, H. Yanming, Z. Liqun, C. Dafu, T. Wei, *Carbohydrate Polymers,* 2007, 69(4), 748.

Scanning Electron Microscope (SEM)

Morphological characterization of HCC—C microcellular foams was performed on images acquired using a SEM, Hitachi S-3200N. The samples were fractured after freezing in a liquid nitrogen bath and then coated with platinum of 10 nm thickness to make the samples conductive. K. El-Tahlawy, R. A. Venditti, J. J. Pawlak, Carbohydrate Polymers, 2007, 67(3), 319.

Contact Angle

Dynamic contact angle measurements were performed with a Phoenix 300 Contact Angle Analyzer (Seo Co., Ltd., Korea) on the HCC—C foams. Deionized water was used as the probe fluid. The time interval for image acquisition was 0.5 seconds and data was collected for about 30 seconds.

Measurement of Tensile Strength

The HCC—C foams were equilibrated in a conditioning room with an atmosphere of 23° C. and 50% relative humidity air for 48 hours. Each sample size was approximately 30×10× 4.1 mm. The tensile strength of the HCC—C foams were measured using an Instron 4411 (Canton, Mass.) tensile testing machine in the same conditioning room. The crosshead speed was 2 mm/second.

Dynamic Mechanical Analysis (DMA)

DMA was performed with DMA Model 2980 (TA Inc, New Castle Del.) in the film-tension mode. Sample dimensions were approximately 30 mm length, 10 mm width and a 3.5 mm thickness. Samples were heated from −50 to 200° C. at 2° C./min (20 um amplitude, 0.67% strain, at 1 Hz). Each sample was measured for length, width and thickness before mounting.

Void Fraction

The void fraction of each sample of HCC—C foam was calculated as one minus the foam density/wall density. The total volume of the foam was determined by placing the foam in a cylinder with known volume and then adding small beads (average diameter of 2.5 mm) to fill the volume. The beads total mass and packing density was also known. By subtracting the volume of the beads, the foam volume was ascertained. The foam density is simply the measured volume divided by the sample mass. The HCC—C cell wall material density was determined by preparing a solid HCC—C sample by oven drying a wet sample after the cross linking reaction, without freeze drying. The volume was measured using a water displacement method. The density was determined simply from the measured volume divided by the sample mass, i.e., 1.1 g/cc.

Formation of Foam Structure

A flexible dry foam was formed via freeze drying from HC-chitosan and HCC—C. FIGS. 7A-7D show a sample of HCC—C foam. The foam could be strained (as shown in FIGS. 7B-7D) and when unstrained the original shape was recovered (FIG. 7A). However, chitosan alone and HCC alone did not form foams upon freeze drying, rather they formed brittle, hard, glass-like materials. It is thus considered that the cross linking between the HCC and chitosan is responsible for the elastic nature of the foam.

Figure 8A:
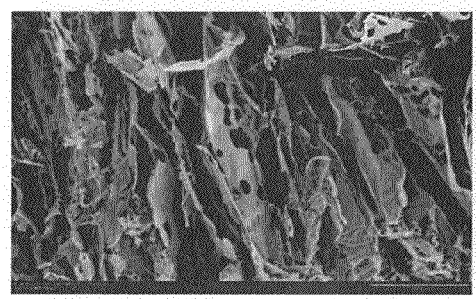
FIG. 8A is an image of hemicellulose-chitosan foam with a length scale of 500 micrometers.
Figure 8B:
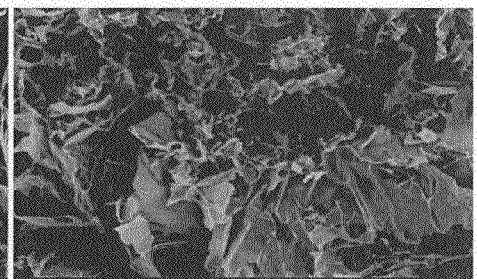
FIG. 8B is an image of hemicellulose citrate-chitosan foam with a length scale of 500 micrometers.
Figure 8C:
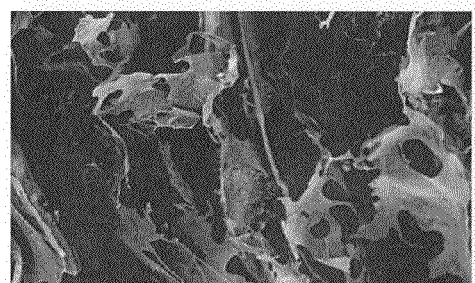
FIG. 8C is an image of the hemicellulose-chitosan foam of FIG. 8A with a length scale of 200 micrometers.
Figure 8D:
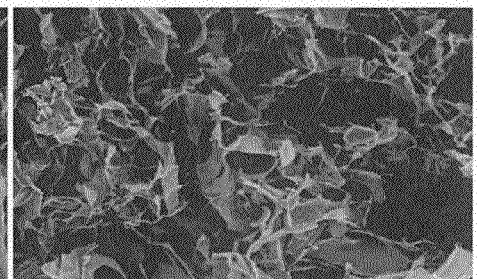
FIG. 8D is an image of the hemicellulose citrate-chitosan foam of FIG. 8B with a length scale of 200 micrometers.
Figure 8E:
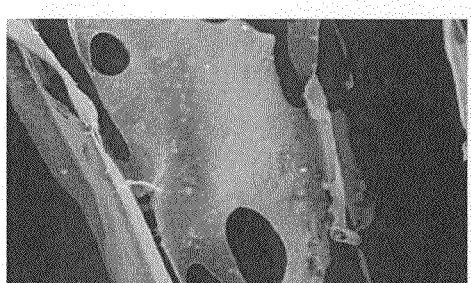
FIG. 8E is an image of the hemicellulose-chitosan foam of FIG. 8A with a length scale of 50 micrometers.
Figure 8F:
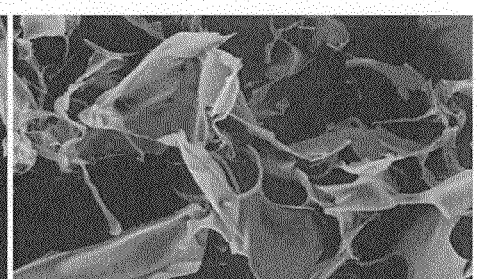
FIG. 8F is an image of the hemicellulose citrate-chitosan foam of FIG. 8B with a length scale of 50 micrometers.

SEM images reveal the structure of the foam as being a connected three dimensional structure with plate like features and a continuous connected pore region. FIGS. 8A and 8B are SEM images of HC-chitosan and HCC—C foams, respectively, with a length scale of 500 micrometers. FIGS. 8C and 8D are SEM images of HC-chitosan and HCC—C foams, respectively, with a length scale of 200 micrometers. FIGS. 8E and 8F are SEM images of HC-chitosan and HCC—C foams, respectively, with a length scale of 50 micrometers. The HCC—C SEM images reveal a smoother surface than does the HC-chitosan blend alone at the highest magnifications shown.

Effect of HCC to Chitosan (HCC:C) Ratio on Properties of HCC—C

Figure 9:
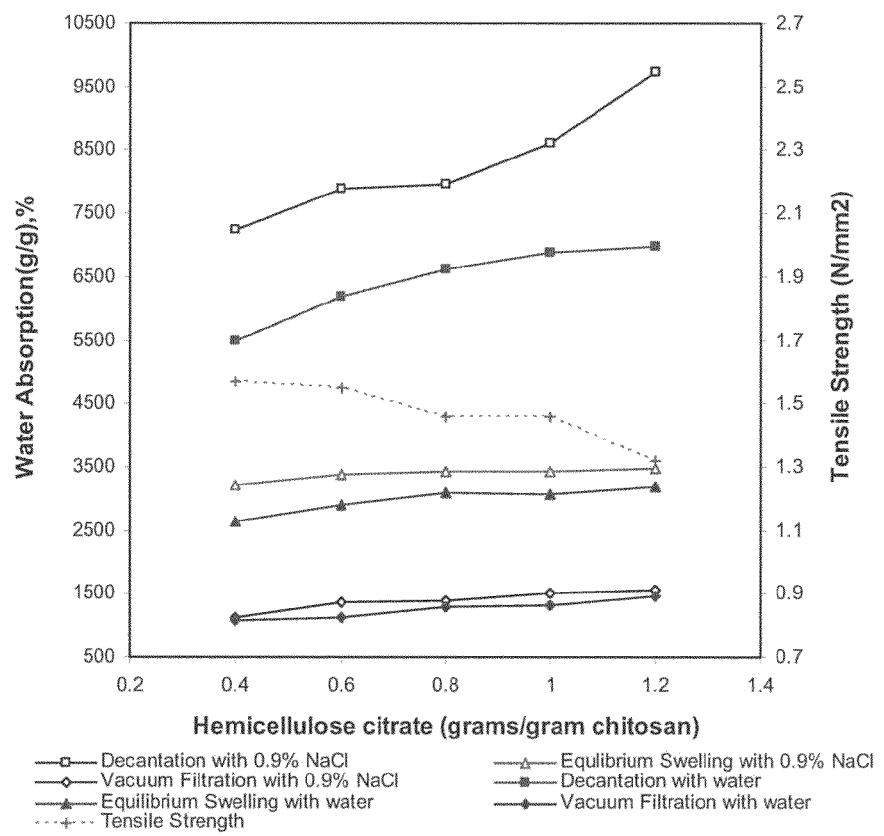
FIG. 9 is a plot showing the effect of hemicellulose citrate concentration on water absorption (one hour of soaking) and tensile strength in hemicellulose citrate-chitosan foam formed under the following reaction conditions: pH=3.5, temperature=100° C., time=3 hours, and a solid to liquid ratio of 1:100.

The effects of the HCC:C ratio (gram/gram) on the absorption and tensile strength of the resulting foams are shown in FIG. 9. The water absorption increases with an increased HCC:C ratio, whereas the strength decreases slightly with an increased HCC:C ratio. Water absorption increases with an increased HCC:C ratio, which may be due to the increased amount of hydrophilic carboxyl groups in the system. From titrations, it was determined that the HCC had approximately 742 milliequivalents per 100 gram of material and the chitosan had 525 milliequivalents per 100 gram of material. This means that at a HCC:C ratio of 0.71, the number of acid groups in the HCC equals the number of amino groups in the chitosan. The absorption properties versus composition continuously increase without significant effect at this stoichiometric ratio.

Interestingly, the water absorption when soaked in the 0.9% NaCl solution was significantly higher than with the deionized water, measured with three different absorption tests. This is unlike conventional superabsorbants, which absorb less saline solution than pure water. This may be explained by the observation that the HCC—C dimensions increased significantly more for the sodium chloride solution than for the de-ionized water. Further, it was plausible that the HCC—C was forming sodium acetate in the sodium chloride solution, increasing the weight.

Figure 10:
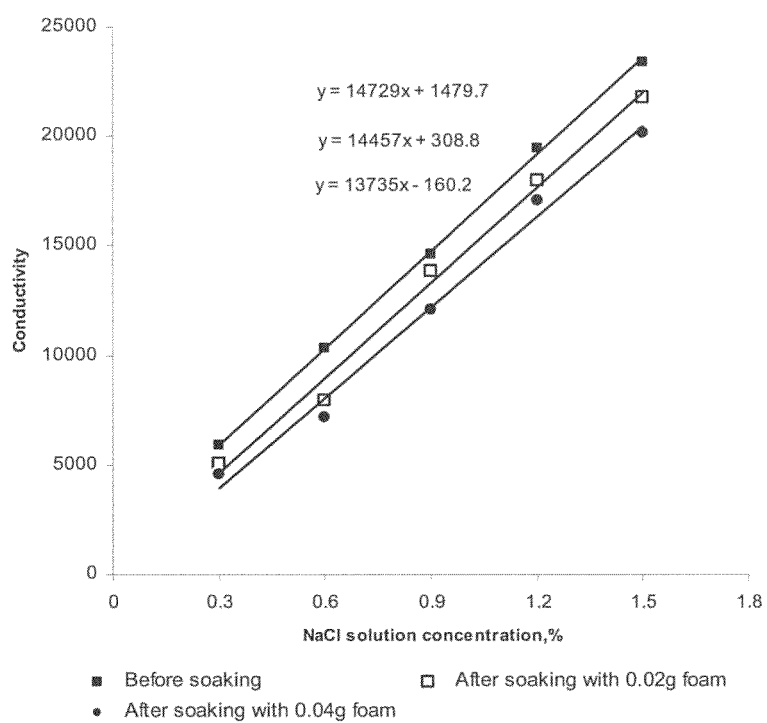
FIG. 10 is a plot showing the conductivity of a sodium chloride solution and the concentration of sodium chloride in the sodium chloride solution before and after soaking 0.02 grams (unfilled squares) and 0.04 grams (circles) of hemicellulose citrate-chitosan foam in 50 ml of sodium chloride solution.

To confirm formation of the sodium acetate, the conductivity of the sodium chloride solution before and after soaking was measured and the results are illustrated in FIG. 10. The decrease in conductivity indicates a decrease in sodium and chloride ion concentration. The weight gain is due to a heterogeneous complex between the carboxylic group of the HCC—C foam and the sodium chloride. The complex with sodium chloride was determined gravimetrically via conventional drying in an oven to be about 11% weight gain on the sample. Additionally, using TGA, it was found that the char of the HCC—C soaked in the NaCl solution weighed approximately 13.5% higher than a control not soaked in NaCl solution. Thus, a 10% increase in weight (saline versus water absorption) is due to the heterogeneous complex, and the cause of weight increases above about 10% is still unexplained.

Table 4 below shows the weight loss and some other properties as a function of the HCC:C ratio. The weight loss passes through a minimum value at a HCC:C ratio of around 0.8:1, near the HCC:C ratio in which there is a stoichiometric ratio of the acid to amine present.

Table 4: Effect of HCC:C ratio on properties. NA indicates that these conditions did not produce a foam product.

TABLE 4

Effect of HCC:C ratio on properties. NA indicates that these conditions did not produce a foam product.

| HCC:C ratio | Temperature (° C.) | pH | Tensile strength (N/mm$^2$) | Weight loss with DI water | Weight loss with 0.9% NaCl solution | Void Fraction |
|---|---|---|---|---|---|---|
| 0.4:1 | 100 | 3.5 | 1.57 | 12.6 | −6.3 | 0.9968 |
| 0.6:1 | | | 1.55 | 11.7 | −7.2 | 0.9970 |
| 0.8:1 | | | 1.46 | 9.6 | −7.9 | 0.9974 |
| 1:1 | | | 1.46 | 7.1 | −9.3 | 0.9976 |
| 1.2:1 | | | 1.30 | 17.4 | 2.4 | 0.9980 |
| 1:1 | 80 | 3.5 | 1.06 | 15.1 | 3.8 | 0.9966 |
| | 90 | | 1.29 | 10.0 | −4.7 | 0.9970 |
| | 100 | | 1.46 | 8.5 | −9.3 | 0.9975 |
| | 110 | | 1.61 | 8.1 | −5.3 | 0.9977 |
| | 120 | | 1.30 | 8.7 | 1.1 | 0.9980 |
| 1:1 | 110 | 2.5 | 0.20 | 42.9 | 37.4 | 0.9922 |
| | | 3.5 | 1.61 | 7.6 | −5.3 | 0.9977 |
| | | 4.5 | 0.79 | 37.8 | 16.1 | 0.9947 |
| | | 5.5 | NA | 40.3 | 59.7 | 0.9735 |

Effect of Cross Linking Temperature on Properties of HCC—C

Figure 11:
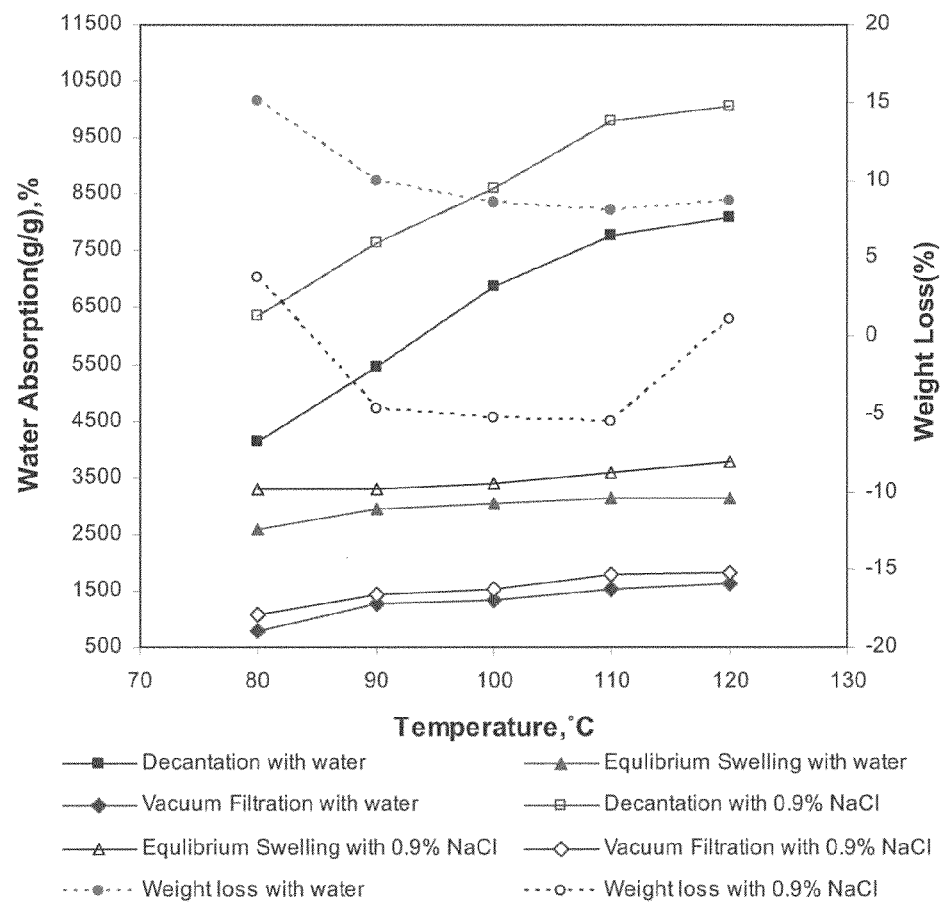
FIG. 11 is a plot showing the effect of different void fractions (wherein the void fraction increases as the reaction temperature increases) on water absorption (one hour of soaking) and weight loss in hemicellulose citrate-chitosan foam formed under the following reaction conditions: pH=3.5, time=3 hours, chitosan to hemicellulose citrate ratio of 1:1 and a solid to liquid ratio of 1:100.

Increases in reaction temperature increased the void fraction, as shown in Table 4, for samples with a 1:1 HCC:C ratio. As illustrated in FIG. 11, the water and saline absorption increased with increased reaction temperature. However, the weight loss of the foam passes through a minimum with increased void fraction. This may be explained by the fact that the highest pore fraction material was produced at 120° C. and at this elevated temperature the foam material thermally degrades and is more brittle and falls apart upon immersion in the saline solution, resulting in greater mass loss.

Effect of pH on properties of HCC—C

Figure 12:
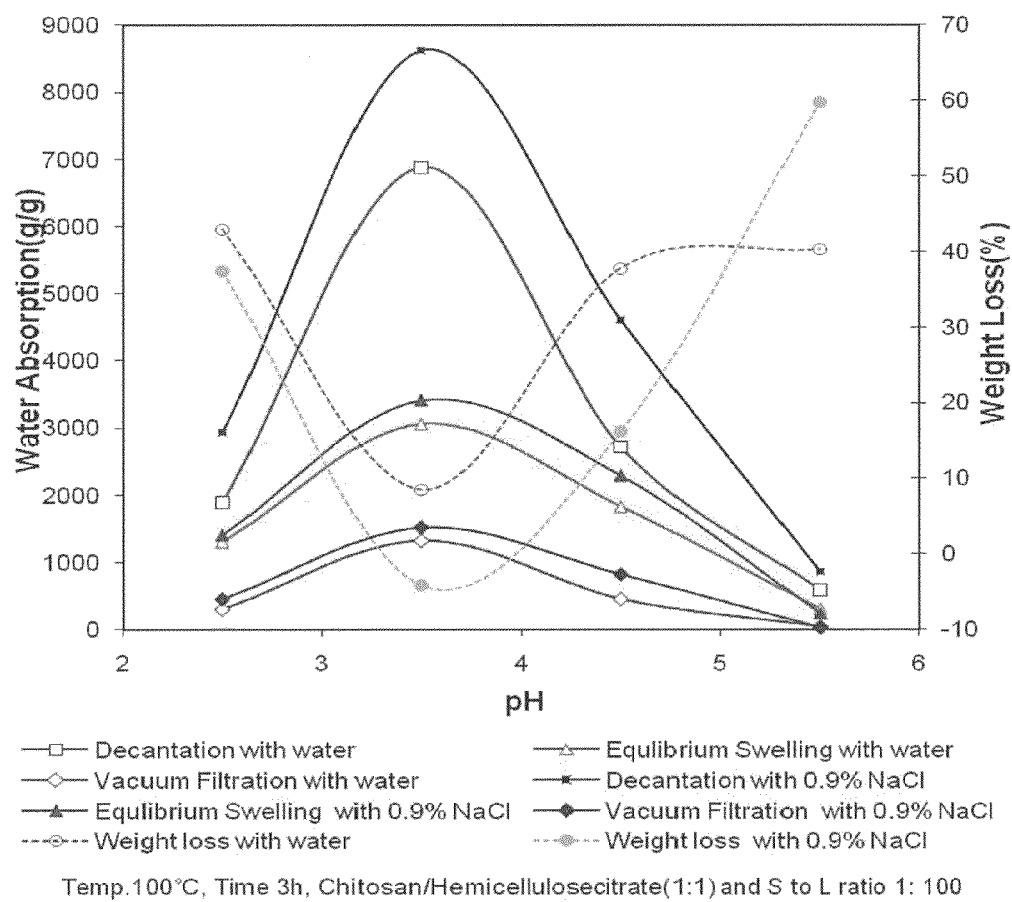
FIG. 12 is a plot showing the effect of pH on water absorption (one hour of soaking) and weight loss in hemicellulose citrate-chitosan foam formed under the following reaction conditions: temperature=100° C., time=3 hours, chitosan to hemicellulose citrate ratio of 1:1 and a solid to liquid ratio of 1:100.

As illustrated in FIG. 12, there was a maximum in water and NaCl solution absorption and a minimum in weight loss with respect to pH at pH=3.5 for samples with a 1:1 HCC:C ratio. This may be explained in that the cross linking of chains occurs due to the inter-chain —NH$_3$+—OOC— salt bonds. P. Bemabé1, C. Peniche, W. Argüelles-Monal, *Polymer Bulletin*, 2005, 55, 367. However, at low or high pH these bonds can be broken, resulting in the disintegration of the polyelectrolyte complex and dissolution of the HCC—C foam.

In addition, the reaction time (0.5 to 3.0 h) and solid to liquid ratio (1:60 to 1:140) was investigated to determine optimum reaction conditions (data not shown). For these experiments, the HCC:C ratio was 1:1, pH=3.5 and the reaction temperature was 110° C. Water and saline absorption increased with reaction time (from 510% to 1550% and 971% to 1760%, respectively, with vacuum filtration method) and solid to liquid ratio (from 630% to 1420% and 1120% to 1360%, respectively, with vacuum filtration method). The weight loss decreased with increased reaction time and generally increased with the increased solid to liquor ratio. The maximum water absorption and minimum weight loss were obtained at 2.5 hours reaction time with solid to liquid ratio of 1:100.

Summary of Cross Linked HC-Chitosan and HCC—C Foam Reaction Results

A summary of results of HCC—C foam relative to several control materials is shown in Table 5. Water absorption with deionized water and NaCl solution, as well as strength are improved with the HCC—C relative to the HC-chitosan (HC—C) control. This may be due to the increased carboxylic groups in the HCC relative to HC that forms covalent amide bonds with the amino chitosan groups. The absorbency of the HCC—C foam was significantly higher than the commercial cellulose foam (void fraction 0.9656) with water and saline solution. This was true even though the void fraction of the commercial cellulose foam of 0.9656 was similar to the HCC—C (in the range of 0.9978). The absorbency of super absorbent powder with DI water was significantly higher than that of the HCC—C. However, the absorbency of super absorbent powder with 0.9% saline solution (decantation method) was comparable to that of HCC—C foam. Volume measurements of the swollen materials confirm the water and saline absorption results in Table 5.

Table 5: Properties of HCC—C foam and other materials. HCC to chitosan mass ratio of 1:1, pH=3.5, Time=2.5 hours, Temperature=110° C. and solid:liquor ratio of 1:100. NA means HCC or chitosan produces a powder, not a foam.

TABLE 5

Properties of HCC-C foam and other materials. HCC to chitosan mass ratio of 1:1, pH = 3.5, Time = 2.5 hours, Temperature = 110° C. and solid:liquor ratio of 1:100. NA means HCC or chitosan produces a powder, not a foam.

| Sample | Density (g/cc) | Water absorption percent with DI water at 1 hr | | | Saline absorption percent with 0.9% NaCl at 1 hr | | | | Weight Loss (%) at 1 hr | | % Volume Expansion[1] | | Tensile Strength (N/mm$^2$) |
|---|---|---|---|---|---|---|---|---|---|---|---|---|---|
| | | Dec | ES | VF | Dec | ES | VF | Load[2] | Water | NaCl | Water | NaCl | |
| HCC-C | 0.00254 | 7800 | 3100 | 1500 | 9800 | 3600 | 1800 | 630 | 8.1 | −9.3 | 110 | 240 | 1.61 |
| HC-C | 0.00572 | 2300 | 800 | 400 | 2400 | 900 | 400 | | 28.6 | 23.7 | | | 0.54 |
| HCC | | 1400 | 500 | 350 | 1500 | 600 | 400 | | 21.0 | 15.6 | | | NA |
| HC | | 600 | 200 | 100 | 700 | 300 | 200 | | 18.5 | 16.2 | | | NA |
| SC-C | 0.00406 | 11300 | 2780 | 1830 | 13960 | 3800 | 2440 | 670 | 7.1 | −10.0 | 200 | 270 | 1.8 |
| S-C | 0.00757 | 2320 | 730 | 530 | 2610 | 720 | 540 | | 20.4 | 14.8 | | | 1.0 |
| S | | 1020 | 800 | 640 | 930 | 730 | 610 | | 23.1 | 16.3 | | | NA |
| Chitosan | | 1200 | 700 | 600 | 1300 | 1000 | 600 | | 53.0 | 41.0 | | | NA |
| Commercial cellulose foam | 0.0378 | 700 | 600 | 200 | 800 | 600 | 300 | 50 | 55.4 | 50.9 | 20 | 40 | 23.8 |
| Super absorbent (acrylic base) | | 24100 | 19700 | 14900 | 4700 | 4200 | 1800 | 1160 | 2.9 | 1.0 | 21000 | 140 | NA |
| Commercial diaper | | | | | 3400 | | 660 | | | | | | |

[1]Volume expansivity equals 100% $(V_{eq} - V_{dry})/V_{dry}$, where V is volume and eq and dry denote liquid swollen and dry states.
[2]Saline solution absorbance under a load of 4.9 psig.

For some absorbency applications, the water holding power of the absorbent versus applied pressure is important, for instance in diaper applications. The HCC—C maintained a 630% saline solution absorbed under loading. This value was similar to starch citrate-chitosan (SC—C) (670%) and a commercial diaper product consisting of wood fibers and superabsorbent (660%). The commercial cellulose sponge had a 50% saline solution absorption under loading. The higher value of HCC—C relative to the cellulose sponge reflects a higher tenacity to hold the liquid, indicating that the chemistry and not just the pore fraction is acting to hold liquids. Superabsorbent alone had an 1160% absorbance under load, indicating a superior liquid holding performance under load relative to the HC or S based citrate-chitosan materials.

As a further comparison between materials, Table 6A lists the conductivity of salt solutions after exposure of the solutions to 0.04 grams of sample and then sample removal. Also, the final concentration of NaCl was measured by weighing a sample of the solution and then drying and weighing the solid residue. As stated before, the conductivity of the solution after exposure to HCC—C decreases and the NaCl concentration decreases, presumably due to a heterogeneous complex between the foam and NaCl. However, for the super absorbent the salt concentration decreases somewhat but the conductivity does not decrease, but slightly increases. For the commercial cellulose sponge, the conductivity increases significantly. This is presumably due to the leaching out of magnesium chloride from the sponge. Table 6B shows conductivities before and after immersion with the absorbents at different initial concentrations of NaCl. The results confirm that the HCC—C foam is the only one to significantly decrease the salt concentrations. Similar experiments were performed with HCl solutions, but no change in conductivity before and after soaking was observed with all three absorbent materials (data not shown).

Table 6A: Effect on salt concentration and conductivity after immersion of 0.04 grams of absorbent into 50 ml saline solutions.

TABLE 6A

Effect on salt concentration and conductivity after immersion of 0.04 grams of absorbent into 50 ml saline solutions.

| Sample | Initial NaCl (g/l) | Final NaCl (g/l) | Initial conductivity (µs/cm) | Final conductivity (µs/cm) |
|---|---|---|---|---|
| HCC-C | 9.0 | 8.5 | 13100 | 10000 |
| Commercial cellulose foam | 9.0 | 9.0 | 13100 | 13800 |
| Super Absorbent | 9.0 | 8.8 | 13100 | 13300 |

Table 6B: Conductivity (µs/cm) after immersion of absorbents into saline solutions. Sample mass was 0.02 grams and the saline solution volume was 50 ml.

TABLE 6B

Conductivity (µs/cm) after immersion of absorbents into saline solutions. Sample mass was 0.02 grams and the saline solution volume was 50 ml.

| Conc. NaCl (g/l) | Blank | Super Absorbent | Commercial Cellulose foam | HCC-C |
|---|---|---|---|---|
| 3 | 4700 | 4820 | 5650 | 4280 |
| 6 | 7670 | 8310 | 8790 | 7190 |
| 9 | 13100 | 14200 | 15800 | 13800 |
| 12 | 19500 | 19800 | 20300 | 18000 |
| 15 | 23100 | 23200 | 24000 | 21800 |

Results of FTIR Analysis

Figure 13:
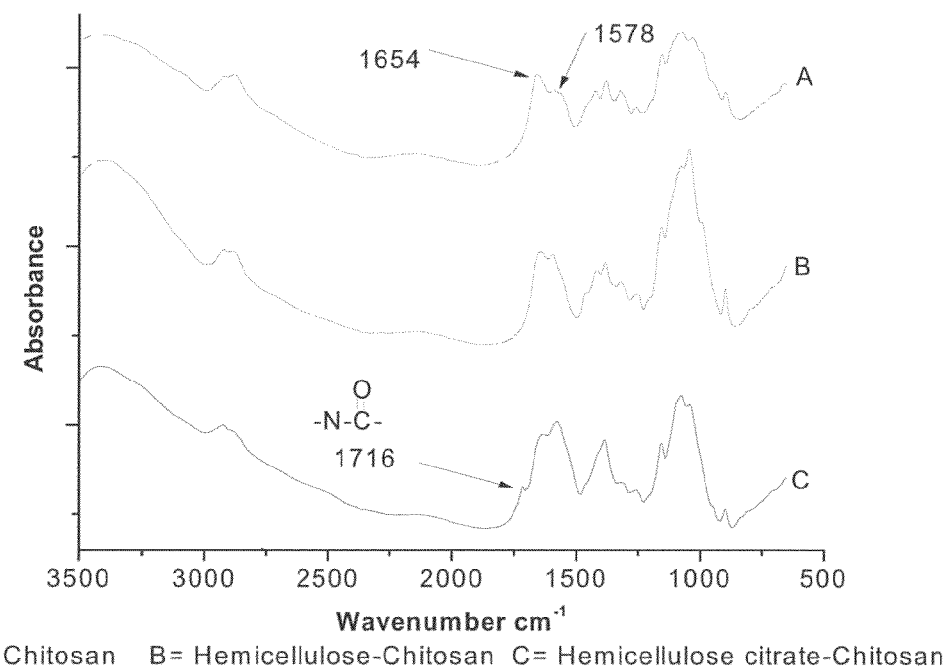
FIG. 13 is a plot of FTIR spectra of chitosan, hemicellulose-chitosan, and hemicellulose citrate-chitosan.

The FTIR spectra of chitosan (A), HC—C (B) and HCC—C(C) are shown in FIG. 13. Analysis of the FTIR data for chitosan (A) showed absorption bands at 1654 and 1578 cm-1, corresponding to amide (I) and amide (II) bands respectively. The bands observed at 3474 cm-1 correspond to the vibrational stretching of the hydroxyl groups. Q. Nie, W. B. Tan, Y. Zhang, *Nanotechnology*, 2006, 17(1), 140. For HCC—C(C), a new peak is observed at 1716 cm-1, attributable to the characteristic stretching band of carbonyl groups of HCC cross linked with chitosan. K. Umemura, S. Kawai, *Applied Polymer Science*, 2008, 108(4), 2481. Thus, it is obvious that the intensity of amine bands for chitosan increased after HCC was incorporated into the chitosan, suggesting that HCC was linked to chitosan via reactions between amino groups of chitosan and carboxylic groups of HCC. D. Alonso, M. Gimeno, R. Olayo, H. Vázquez-Torres, J. D. Sepúlveda-Sánchez, K. Shirai, *Carbohydrate Polymers*, 2009, 77(3), 536; J. Yin, K. L. Kun, X. Chen, V. V. Khutoryanskiy, *Carbohydrate Polymers*, 2006, 63(2), 238; U. Edlund, *Bioactive and Compatible Polymers*, 2008, 23(2), 171.

Thermogravimetric Results

The thermogravimetric results of HCC—C, HC—C, HCC, HC and chitosan are shown in Table 7. The residual char and maximum in the DTG of HCC—C foam was higher, indicating a more cross linked structure. The maximum in the DTG of the HCC was significantly lower than the HC and chitosan, attributable to the citric acid being a plasticizer, with a melting point of 158.5° C. The maximum in the DTG of CA is 191.4° C. The chitosan endothermic peak was significantly higher than all of the other materials. TGA results from saline soaked HCC—C indicate NaCl absorption of 0.135 grams/gram.

Table 7: Thermal behavior of foams.

TABLE 7

Thermal behavior of foams.

| Sample | TGA maximum (DTG) degradation temp. (° C.) | Residual char at 600° C. (%) | DSC Endothermic Peak (° C.) |
|---|---|---|---|
| HCC-C | 296 | 28.3 | 183 |
| HC-C | 293 | 25.0 | 186 |
| HCC | 202 | 32.5 | 188 |
| HC | 289 | 21.8 | 192 |
| Chitosan | 295 | 26.8 | 269 |

Results of Elemental Analysis

As set forth in Table 8, elemental analysis shows 7.2% nitrogen in the chitosan. For the repeat unit of chitosan, the nitrogen content ideally should be 14/161 or 8.7%. The nitrogen content for chitin should be 203/14 or 6.9%. This indicates that this chitosan is not completely deacetylated. In fact, the manufacturer claims a % deacetylation between 75 and 85%. When the chitosan was blended with HC or HCC, the nitrogen % decreased approximately by one-half, indicating that there are no mass losses accompanying reactions when these materials are blended and reacted.

Table 8: Elemental analysis of chitosan, HC—C and HCC—C

TABLE 8

Elemental analysis of chitosan, HC-C and HCC-C

| Sample | % C | % H | % N | % O |
|---|---|---|---|---|
| Chitosan | 40.2 | 7.3 | 7.2 | 45.2 |
| HC-C | 37.0 | 6.6 | 3.9 | 52.3 |
| HCC-C | 37.2 | 6.4 | 3.5 | 53.0 |

Results of Dynamic Contact Angle with Water

Figures 14A, 14B:
FIG. 14A is an image of the contact angle of water at 0.5 seconds on hemicellulose-chitosan foam.
FIG. 14B is an image of the contact angle of water at 10.0 seconds on the hemicellulose-chitosan foam of FIG. 14A.
Figures 14C, 14D:
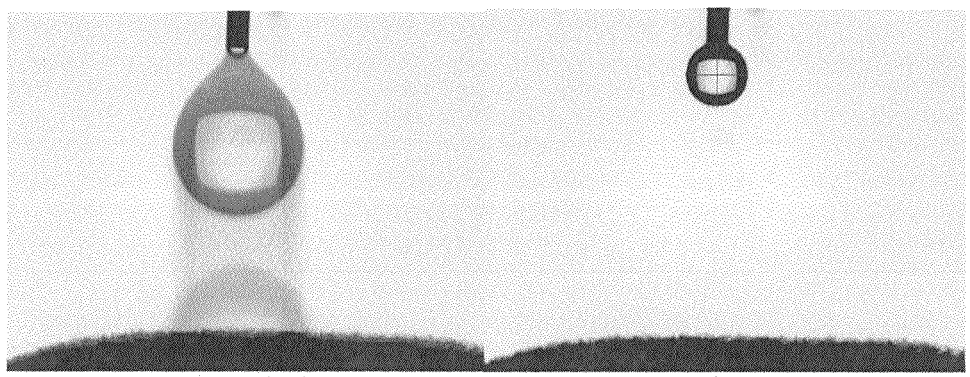
FIG. 14C is an image of the contact angle of water at 0.0 seconds on hemicellulose citrate-chitosan foam.
FIG. 14D is an image of the contact angle of water at 0.5 seconds on the hemicellulose citrate-chitosan foam of FIG. 14C.

The dynamic contact angle with DI water measured at 0.5 seconds of contact time was determined to be 85° for HC—C foam. The water drop remained for approximately 10 seconds. In contrast, the dynamic contact angles with DI water at 0.5 seconds for HCC—C foams was 0° and the drop was fully absorbed in 0.5 seconds. This reflects the significantly increased absorbency of the HCC—C foam relative to the HC—C foam. The short time contact angle of water on the HC—C is attributed to the roughness of the surface. FIG. 14A is an image of the contact angle of water at 0.5 seconds on HC—C foam, and FIG. 14B is an image of the contact angle of water at 10.0 seconds on the HC—C foam of FIG. 14A. FIG. 14C is an image of the contact angle of water at 0.0 seconds on HC—C foam, and FIG. 14D is an image of the contact angle of water at 0.5 seconds on the HCC—C foam of FIG. 14C.

Results of Dynamic Mechanical Analysis (DMA)

Figure 15:
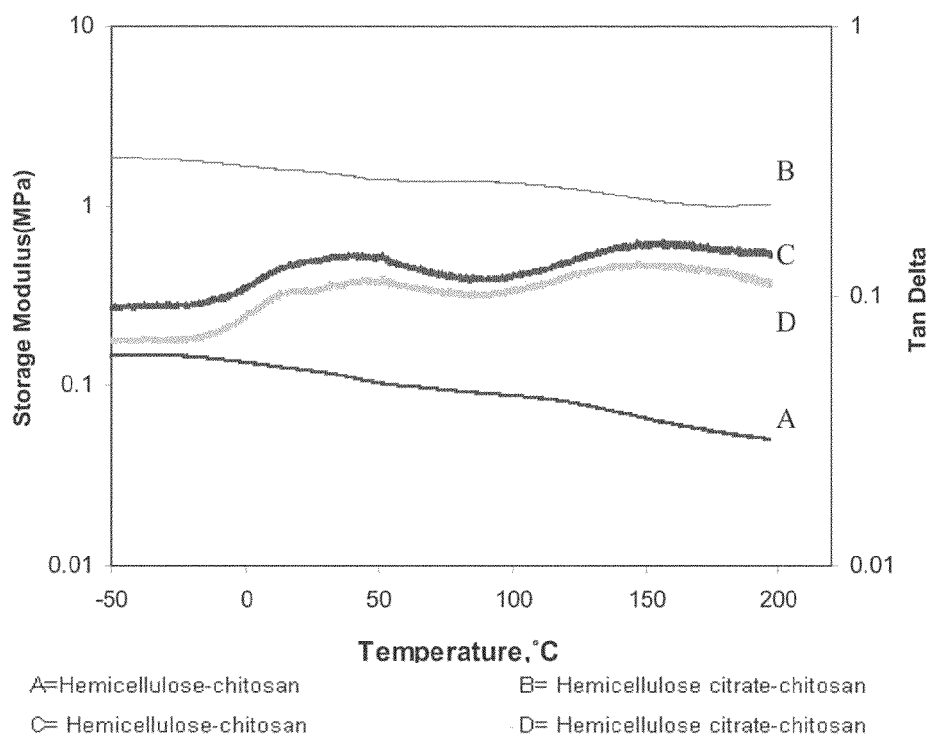
FIG. 15 is a plot of the dynamic mechanical analysis of hemicellulose-chitosan and hemicellulose citrate-chitosan foams.

DMA curves in tension mode with a maximum strain of 0.67% from −10° to 200° C. at 2° C./minute at 1 Hz were acquired of HCC—C foam and HC—C foam, and the results are illustrated in FIG. 15. The storage modulus of HCC—C and HC—C foam both decrease with increased temperature. The storage modulus of HCC—C foam was significantly higher than that of HC—C foam and the tan delta lower, reflecting increased cross links of the HCC to chitosan relative to the HC to chitosan. Two transitions are apparent in both materials, the first spanning 0 to 50° C. and the second from 100 to 200° C. For HCC—C, the lower peak appears to actually be two peaks overlapping. The elastic behavior at room temperature is in agreement with the transitions above and below room temperature.

Conclusions

HCC—C cross linked foams may be synthesized by reacting HCC and chitosan in an aqueous medium. The incorporation of carboxylic acid groups into HC via reaction with CA, followed by cross linking with chitosan greatly improves the properties relative to HC—C alone. The cross linked HCC—C foam has significantly increased water and saline absorption and strength, and decreased weight loss compared to HC—C foam. Optimum conditions with respect to absorption and weight loss for the cross linking of the HCC—C include a 2.5 hour reaction time at 110° C. with pH=3.5, a solid to liquid ratio of 1:100 and a HCC:C ratio of 1:1 (wt/wt). Instrumental analysis of the HCC—C foams confirms the cross linked and hygroscopic behavior of the HCC—C.

EXAMPLE 4

In the present Example, experimental results are presented associated with the synthesis of a starch derivative (i.e., starch citrate (SC)) by the reaction of S with CA in the presence of SHP in a semi-dry oven method. The synthesized SC was cross linked with chitosan (SC—C) in an aqueous medium and absorbent foams were produced. Cross linking reaction conditions affected the water and saline absorbency, weight loss in water and saline solution, and strength of the cross linked product.

Material

Corn starch was supplied by Cargill Incorporated, Minneapolis, Minn., lot # C3J121B. The corn starch is comprised of approximately 25% amylose and 75% amylopectin. The chitosan was purchased from Sigma-Aldrich, St Louis, Mo. (CAS registry number 9012-76-4, medium molecular weight, degree of deacetylation 75-85%). Chemicals of reagent grade utilized were SHP, CAS registry number 123333-67-5; CA, CAS registry number 77-92-9; sodium chloride; acetic acid; and sodium acetate from Fisher Scientific, Fair Lawn, N.J. Whatman filter paper (quantitative number 4, 110 mm diameter) from Whatman International Ltd, Maidstone, England and deionized water were used throughout. A superabsorbent material (particle size 0.8-1 mm, Small Polymer) based on poly acrylic acid (Watersorb, Fayetteville, Ark.) and commercial cellulose foam Spontex (Mapa Spontex Inc. Columbia, Tenn.) were also used as controls.

Synthesis of Starch Derivative with CA in Semi-Dry Oven

CA (5 g) and SHP (1 g) were dissolved in a minimal amount of water (6 ml) in a beaker. Uncooked starch (5 g air dried) was combined with the CA solution in a 100 ml glass beaker and mixed vigorously with a glass rod. The mixture was placed in a forced air oven to dehydrate at 100° C. for 30 min. At this point, all surface moisture was removed and the starch particles were coated with CA. The oven temperature was increased to 120° C. (ramp took about 5 minutes) and the material was allowed to react for 6 hours. The times and temperatures for reaction were determined from several previous trial experiments in which times and temperatures were varied. R. E. Wing, Starch-Starke, 1996, 48, 275. SC reaction products were slurried in water (60 ml) for 30 min, adjusted to pH=2 using acetic acid, filtered on filter paper, and washed with water (60, 120 and 120 ml successive water baths for 30 min) The product was air dried overnight, and the material weighed to determine yield. The proposed reaction scheme is shown above in Example 1.

Optimization of Cross Linking Conditions

For selection of SC concentration, separately five 100 ml samples were prepared with 0.4, 0.6, 0.8, 1.0 and 1.2% SC with DI water. A chitosan solution was prepared by adding 1 grain of chitosan to a mixture of 99 ml of water and 1 ml of glacial acetic acid. The chitosan solution was added to each of the SC samples at a ratio of 1:1 in a 500 ml round bottom flask. The proposed cross linking reaction scheme of SC with chitosan is shown below:

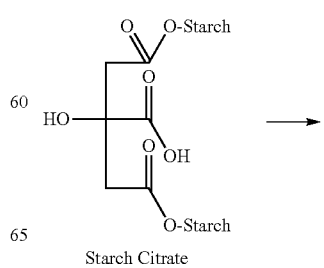

Starch Citrate

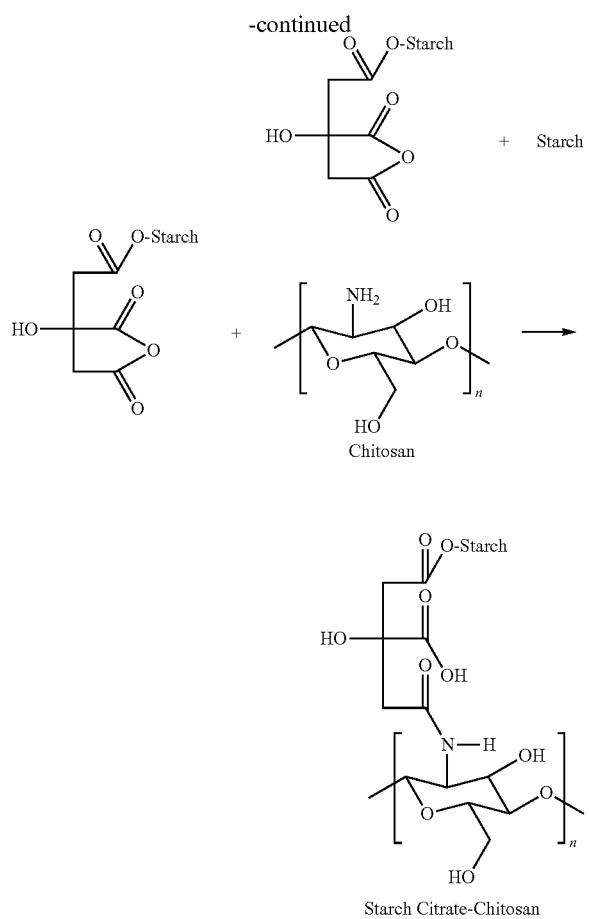

Starch Citrate-Chitosan

The pH was then adjusted to 4 with sodium acetate. The reaction mixture was stirred using a magnetic stirrer at a fixed temperature using an oil bath (100° C.) and fixed time (3 hours), followed by ambient cooling to room temperature (for approximately one hour) and then the product was freeze dried (Free Dryer System Vacuum Pump, Labconco Corporation, Kansas, Mo.) to create a foam. The percent of SC at which maximum water absorption and minimum weight loss obtained was selected. Further, reaction time (1 to 3 h), reaction temperature (80 to 120° C.), pH (3 to 6) and solid to liquid ratio (1:60 to 1:140) were investigated similarly. For the study of reaction temperature, reactions above 100° C. were conducted in a glass container held inside a bomb digester. It was determined that performing the reaction at above 100° C. inside a steel container did not produce a useful foam due to an interference of the metal with cross linking; the strength of these products was very low and the foam products dissolved when immersed in water.

Measuring Water Absorbency and Weight Loss

The decantation, equilibrium swelling, and vacuum filtration methods described in Example 3 were used to determine water absorption and weight loss of SC—C samples.

Characterization of SC—C Samples

FTIR spectra, thermogravimetric behavior, DSC analysis, morphological characterization, DMA, dynamic contact angle analysis, and tensile strength analysis were all performed on SC—C samples as described above in Example 3.

Cross polarized magic angle spinning nuclear magnetic resonance (CP: MAS NMR) spectra were obtained for SC—C and chitosan powders using a Bruker 500 instrument operating at 75.4 MHz for $^{13}$C. Powdered samples were packed in two 3.2 mm rotors and spun at 4000 Hz. Air-tight end caps were used on the rotors. The contact time and recycle delay were 2 ms and 1 s, respectively. Good signal to noise ratios were obtained by accumulating 1100-2000 scans. Spinning sidebands were suppressed by applying the total suppression of sidebands (TOSS) pulse sequence. L. P. Bail, G. F. Morin, H. R. Marchessault, *International J. of Biological Macromolecules*, 1999, 26, 193.

Formation of Foam Structure

Figures 16A, 16B:
FIG. 16A is an image of a sample of starch-chitosan foam, where the Petri dish size is 100 mm in diameter, with a 15 mm lip height.
FIG. 16B is an image of a sample of starch citrate-chitosan foam, where the Petri dish size is 100 mm in diameter, with a 15 mm lip height.
Figures 17A, 17B:
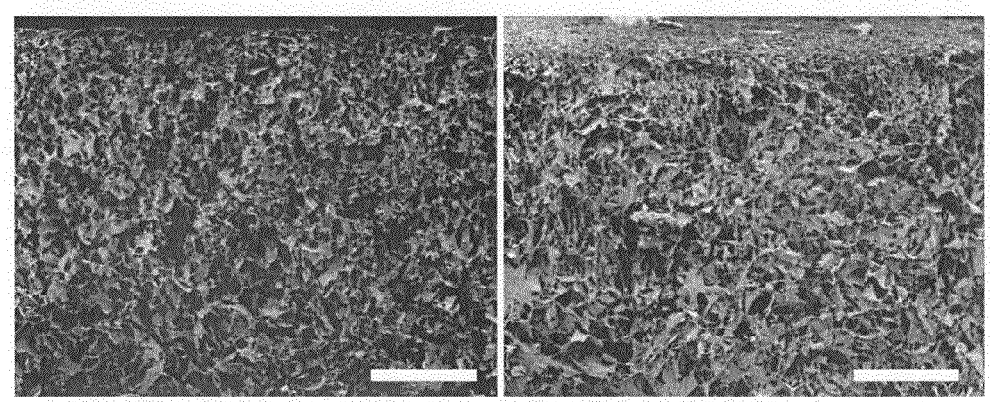
FIG. 17A is an image of starch-chitosan foam with a length scale of 500 micrometers.
FIG. 17B is an image of starch citrate-chitosan foam with a length scale of 500 micrometers.
Figures 17C, 17D:
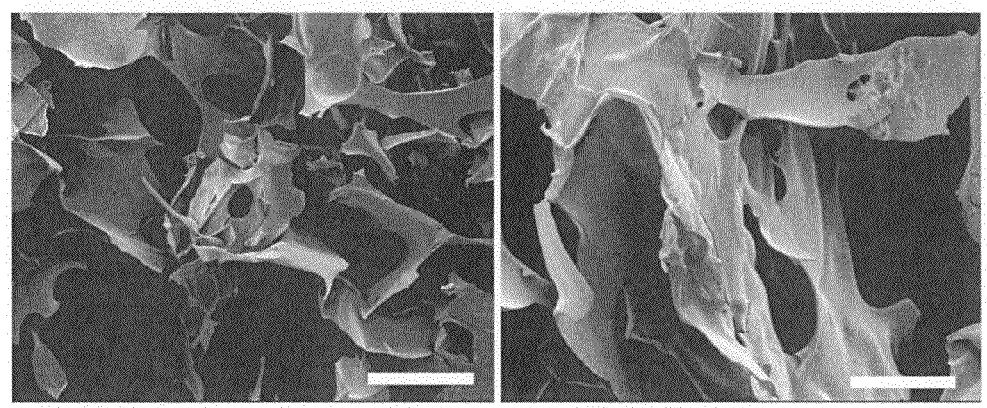
FIG. 17C is an image of the starch-chitosan foam of FIG. 17A with a length scale of 50 micrometers.
FIG. 17D is an image of the starch citrate-chitosan foam of FIG. 17B with a length scale of 50 micrometers.

Examples of starch-chitosan (S—C) foam and SC—C foam are shown in FIGS. 16A and 16B, respectively. Scanning electron microscopy of the freeze dried samples shows a continuous irregular pore structure with plate like solid pore walls, as can be seen in FIGS. 17A-17D. FIG. 17A is an image of S—C foam with a length scale of 500 micrometers, and FIG. 17B is an image of SC—C foam with a length scale of 500 micrometers. FIG. 17C is an image of the S—C foam of FIG. 17A with a length scale of 50 micrometers, and FIG. 17D is an image of the SC—C foam of FIG. 17B with a length scale of 50 micrometers.

The void fraction of the SC—C foams was determined by the foam density and from the cell wall SC—C material density which was determined to be 1.1 g/cm$^3$. The pore-free material that was considered to be similar to the cell wall was prepared by drying a 100 ml water based SC—C solution in an oven at 105° C. overnight. The dried glassy transparent material had no detected voids. The density was determined from the mass and volume (by a water displacement measurement), measured in triplicate.

From manual manipulation, the foams were found in most cases to be elastic. A somewhat brittle, weak foam was formed from starch alone, however the foam was so weak that tensile tests could not be performed on it. In contrast, neither chitosan nor SC alone formed foams upon freeze drying.

Effect of Cross Linking Reaction Time on Properties of SC—C

As the reaction time increased, the void fraction, strength, and water and NaCl solution absorption increased and the weight loss decreased, as summarized in Table 9 below. This is consistent with prolonged treatment times producing more SC—C amide covalent bonds. Interestingly, there is an observed weight increase of the samples after immersion in NaCl solution, indicating formation of sodium acetate and a minimal solubility of the carbohydrate material after soaking. TGA experiments of the sample with 3.0 hour reaction time before and after soaking in a NaCl solution for one hour showed that there was about a 10% increase in the residual char (after ramping at 10° C./min to 600° C.) for the soaked material, attributable to the formation of sodium acetate. Further, SC—C was found to absorb about 10% of its weight of NaCl when immersed in a bath; this was measured by gravimetrically determining the salt in a solution before and after soaking.

Table 9: Effect of cross linking reaction time between SC and chitosan on the absorption, weight loss and strength of SC—C foam (Reaction conditions: SC to Chitosan mass ratio of 1:1, pH=4, Temp.=100'C and Solid:Liquid ratio of 1:100).

TABLE 9

Effect of cross linking reaction time between SC and chitosan on the absorption, weight loss and strength of SC-C foam (Reaction conditions: SC to Chitosan mass ratio of 1:1, pH = 4, Temp. = 100° C. and Solid:Liquid ratio of 1:100).

| Reaction Time (hr) | Tensile Strength (N/mm²) | Void fraction | Absorption Time (hr) | Absorption (%) with DI water | | | Absorption (%) with 0.9% NaCl solution | | | Weight loss (%) | |
|---|---|---|---|---|---|---|---|---|---|---|---|
| | | | | Dec | ES | VF | Dec | ES | VF | Water | NaCl |
| 1.0 | 0.70 | 0.9932 | 0.5 | 2540 | 990 | 540 | 2870 | 1120 | 990 | 2.7 | −7.3 |
| 1.5 | 0.72 | 0.9934 | | 2870 | 1020 | 840 | 3430 | 1280 | 1090 | 2.8 | −10.9 |
| 2.0 | 0.78 | 0.9945 | | 3500 | 1120 | 1050 | 3760 | 1380 | 1330 | 1.9 | −11.3 |
| 2.5 | 0.91 | 0.9951 | | 4130 | 1330 | 1100 | 4050 | 1440 | 1420 | 1.8 | −14.7 |
| 3.0 | 1.44 | 0.9963 | | 4180 | 1470 | 1200 | 4900 | 1670 | 1480 | 1.5 | −14.2 |
| 1.0 | | | 1.0 | 2460 | 1070 | 1100 | 2730 | 1640 | 1420 | 5.9 | −14.8 |
| 1.5 | | | | 3100 | 1170 | 1220 | 4620 | 1700 | 1500 | 5.7 | −14.7 |
| 2.0 | | | | 3400 | 1380 | 1260 | 5180 | 1900 | 1860 | 4.6 | −13.9 |
| 2.5 | | | | 4430 | 1820 | 1270 | 5440 | 1980 | 1870 | 5.5 | −16.4 |
| 3.0 | | | | 4480 | 1940 | 1320 | 6770 | 2430 | 1910 | 4.3 | −12.7 |
| 1.0 | | | 48 | 2980 | 1140 | 1000 | 5880 | 1930 | 1780 | 7.6 | −11.3 |
| 1.5 | | | | 3090 | 1280 | 1100 | 5950 | 2430 | 1830 | 6.3 | −13.4 |
| 2.0 | | | | 3420 | 1300 | 1160 | 6250 | 3050 | 2030 | 6.7 | −14.7 |
| 2.5 | | | | 4460 | 1880 | 1220 | 6260 | 3090 | 2030 | 6.5 | −16.3 |
| 3.0 | | | | 4480 | 1900 | 1390 | 7340 | 3220 | 2190 | 7.1 | −15.7 |

Dec = Decantation, ES = Equilibrium Swellability, VF = Vacuum Filter

Effect of SC to Chitosan (SC:C) Ratio on Properties of SC—C

To investigate the effect of the SC:C ratio, the concentration of SC was varied and the amount of chitosan was fixed. From titrations, it was determined that the carboxylic group concentrations on the SC were 4.9 milliequivalent per gram. The chitosan contained 5.2 milliequivalent of amino groups per gram. This indicates that the mass ratios of SC to chitosan were approximately equal to their reactive group functionality. The water absorption and void fraction increased with increased SC concentration whereas the tensile strength decreased. It is expected with increased void fraction that the strength per unit volume would decrease and mass loss (assumed to increase with increased specific surface area) would increase. The increased ratio of carboxylic acid to amino groups has an effect on the properties of the SC—C but the reasons why are not fully understood. Table 10 below summarizes the effect of the SC:C ratio on various properties of SC—C.

Table 10: Effect of SC:C on the absorption, weight loss and strength of SC—C (Reaction conditions: pH=4, Time=3 hours, Temp.=100° C. and Solid:Liquid Ratio of 1:100).

TABLE 10

Effect of SC:C on the absorption, weight loss and strength of SC-C (Reaction conditions: pH = 4, Time = 3 hours, Temp. = 100° C. and Solid:Liquor ratio of 1:100).

| SC:C ratio | Tensile strength (N/mm²) | Void fraction | Absorption Time (hr) | Absorption (%) with DI water | | | Absorption (%) with 0.9% NaCl solution | | | Weight loss (%) | |
|---|---|---|---|---|---|---|---|---|---|---|---|
| | | | | Dec | ES | VF | Dec | ES | VF | Water | NaCl |
| 0.4 | 1.61 | 0.9913 | 0.5 | 2350 | 1290 | 950 | 2930 | 1380 | 1000 | 2.7 | −22.8 |
| 0.6 | 1.60 | 0.9934 | | 2790 | 1570 | 1000 | 3370 | 1580 | 1140 | 2.4 | −21.2 |
| 0.8 | 1.44 | 0.9944 | | 4130 | 1750 | 1030 | 3720 | 1740 | 1170 | 2.8 | −15.0 |
| 1.0 | 1.16 | 0.9963 | | 4180 | 1760 | 1100 | 4900 | 1870 | 1470 | 1.5 | −14.2 |
| 1.2 | 1.06 | 0.9967 | | 4250 | 1870 | 1220 | 7800 | 2460 | 2160 | 7.8 | 2.6 |
| 0.4 | | | 1.0 | 3240 | 1300 | 1150 | 4230 | 1860 | 1330 | 5.9 | −21.4 |
| 0.6 | | | | 3670 | 1800 | 1200 | 4420 | 2090 | 1450 | 5.1 | −18.4 |
| 0.8 | | | | 4170 | 1860 | 1240 | 4930 | 2170 | 1490 | 5.2 | −13.1 |
| 1.0 | | | | 4480 | 1940 | 1320 | 6770 | 2430 | 1910 | 4.3 | −12.8 |
| 1.2 | | | | 4550 | 1990 | 1360 | 10570 | 3020 | 2760 | 23.1 | 2.8 |
| 0.4 | | | 48 | 3110 | 1340 | 940 | 4460 | 1910 | 1570 | 5.6 | −18.4 |
| 0.6 | | | | 3740 | 1920 | 1100 | 6690 | 2050 | 1680 | 5.8 | −17.6 |
| 0.8 | | | | 4320 | 1980 | 1280 | 6980 | 2350 | 1750 | 9.2 | −15.5 |
| 1.0 | | | | 4480 | 2000 | 1390 | 7340 | 3220 | 2190 | 7.1 | −15.7 |
| 1.2 | | | | 4470 | 1910 | 1200 | 14030 | 3930 | 3520 | 26.4 | 3.5 |

Effect of Solid:Liquid Ratio on Properties of SC—C

As the solid:liquid ratio decreases, the void fraction increases due to the higher volume of liquid that is removed during freeze drying. The result is a more porous, thinner walled foam. Below a solid:liquid ratio of 1:100, it was observed that the foam structure upon immersion in water or the NaCl solution would break, but above this ratio it would not. The tensile strength decreases significantly below the 1:100 solid:liquid ratio and the weight loss increases with decreased solid:liquid ratio, both indicative of a thinner walled, higher surface area foam structure, and in agreement with the observations of breakage in liquids. The water absorption data is somewhat complicated with the decantation method, the least stressful water absorption test, as an increase of absorption is observed with decreased solid:liquid ratio. However, with the other two methods, the absorption appears to pass through a maximum, possibly due to the less integral foam structure. The data also suggests that the decrease in strength may be due to lower cross links as the cross linking agents are effectively diluted in volume with the higher amounts of liquid. Note that negative weight losses are indicative of NaCl absorption into the SC—C sample. Table 11 below summarizes the effect of the solid:liquid ratio of various properties of SC—C.

Table 11: Effect of solid:liquid ratio on absorption and weight loss of SC—C (Reaction conditions: SC:C mass ratio of 1:1, Time=3 hours, Temperature=100° C. and pH=4)

Effect of pH on Properties of SC—C

The effect of pH on the properties of the SC—C samples is shown in Table 12 below. There appears to be a maximum in tensile strength, void fraction, water and NaCl solution absorption and a minimum in weight loss at pH=4. This may be explained in that the cross linking of chains occurs due to the inter-chain —NH$_3$+—OOC— salt bonds. However, at low or high pH these bonds can be broken, resulting in the disintegration of the polyelectrolyte complex and dissolution of the SC—C foam. P. Bernabé1, C. Peniche, W. Argüelles-Monal, *Polymer Bulletin,* 2005, 55, 367. Very high weight losses at higher pH values indicate very low cross linking in these samples.

Table 12: Effect of pH on the absorption, weight loss and strength of SC—C (Reaction conditions: SC:C mass ratio of 1:1, Time=3 hours, Temperature=100° C. and Solid:Liquid Ratio of 1:100).

TABLE 11

Effect of solid:liquid ratio on absorption, weight loss and strength of SC-C (Reaction conditions: SC:C mass ratio of 1:1, Time = 3 hours, Temperature = 100° C. and pH = 4).

| Solid liquid ratio | Tensile strength (N/mm$^2$) | Void fraction | Absorption Time (hr) | Absorption (%) with DI water | | | Absorption (%) with 0.9% NaCl solution | | | Weight loss (%) | |
|---|---|---|---|---|---|---|---|---|---|---|---|
| | | | | Dec | ES | VF | Dec | ES | VF | Water | NaCl |
| 1:60  | 1.34 | 0.9938 | 0.5 | 3250 | 1240 | 680  | 5090 | 1990 | 1120 | 0    | −23.5 |
| 1:80  | 1.33 | 0.9952 |     | 3630 | 1630 | 990  | 6330 | 2510 | 1620 | 0    | −16.7 |
| 1:100 | 1.44 | 0.9963 |     | 4180 | 1660 | 1200 | 6400 | 2670 | 1760 | 1.5  | −14.2 |
| 1:120 | 0.93 | 0.9966 |     | 4110 | 1920 | 1430 | 6600 | 2990 | 1870 | 2.9  | −13.1 |
| 1:140 | 0.70 | 0.9968 |     | 6520 | 1010 | 950  | 6690 | 1380 | 1030 | 6.9  | −11.9 |
| 1:60  |      |        | 1.0 | 3640 | 1650 | 860  | 6690 | 2730 | 1500 | 3.3  | −20.0 |
| 1:80  |      |        |     | 4000 | 2150 | 1190 | 7920 | 3290 | 2070 | 4.0  | −15.4 |
| 1:100 |      |        |     | 4480 | 2230 | 1320 | 8170 | 2430 | 2110 | 4.3  | −12.8 |
| 1:120 |      |        |     | 5500 | 2530 | 1860 | 8700 | 3770 | 2330 | 5.4  | −9.5  |
| 1:140 |      |        |     | 7870 | 1060 | 910  | 8860 | 1220 | 930  | 19.5 | 6.9   |
| 1:60  |      |        | 48  | 3670 | 1600 | 1060 | 6280 | 3420 | 1590 | 2.8  | −17.6 |
| 1:80  |      |        |     | 5300 | 2530 | 1570 | 7630 | 3450 | 2090 | 6.9  | −16.5 |
| 1:100 |      |        |     | 5480 | 2900 | 1680 | 7840 | 3220 | 2190 | 7.1  | −15.7 |
| 1:120 |      |        |     | 6320 | 3130 | 1770 | 6600 | 3250 | 2000 | 11.3 | −8.5  |
| 1:140 |      |        |     | 6050 | 690  | 290  | 4250 | 950  | 260  | 22.1 | 8.1   |

TABLE 12

Effect of pH on absorption, weight loss and strength of SC-C (Reaction conditions: SC:C mass ratio of 1:1, Time = 3 hours, Temperature = 100° C. and Solid:Liquid Ratio of 1:100).

| pH | Tensile Strength (N/mm$^2$) | Void fraction | Absorption Time (hr) | Absorption (%) with DI water | | | Absorption (%) with 0.9% NaCl solution | | | Weight loss (%) | |
|---|---|---|---|---|---|---|---|---|---|---|---|
| | | | | Dec | ES | VF | Dec | ES | VF | Water | NaCl |
| 3 | 1.26 | 0.9958 | 0.5 | 3150 | 1190 | 840 | 3390 | 1470 | 1200 | 6.6 | −3.8 |
| 4 | 1.44 | 0.9963 | | 4170 | 1460 | 1200 | 4900 | 1670 | 1480 | 1.4 | −14.2 |
| 5 | 0.52 | 0.9958 | | 4080 | 1550 | 1120 | 4870 | 2100 | 1430 | 24.9 | 3.6 |
| 6 | 0.10 | 0.9446 | | 2030 | 600 | 450 | 1740 | 1370 | 1110 | 83.8 | 74.1 |
| 3 | | | 1.0 | 4630 | 1600 | 1090 | 5930 | 1970 | 1550 | 5.7 | −7.5 |
| 4 | | | | 5480 | 1940 | 1320 | 6770 | 2430 | 1910 | 4.3 | −12.8 |
| 5 | | | | 5390 | 1890 | 1150 | 6420 | 1830 | 1800 | 27.0 | 12.9 |
| 6 | | | | 2300 | 350 | 190 | 1740 | 330 | 120 | 88.5 | 73.2 |
| 3 | | | 48 | 3050 | 1130 | 800 | 5390 | 2380 | 1940 | 8.5 | −7.3 |
| 4 | | | | 4480 | 1900 | 1390 | 7340 | 3220 | 2190 | 7.1 | −15.7 |
| 5 | | | | 4160 | 1730 | 1360 | 5320 | 2590 | 2020 | 27.4 | 15.3 |
| 6 | | | | 2270 | 250 | 180 | 3170 | 470 | 250 | 87.3 | 74.5 |

Effect of Reaction Temperature on Properties of SC—C

With respect to reaction temperature, the weight loss decreased and the absorption of water and NaCl solution increased, and the strength increased with increased temperature, as can be seen in Table 13 below. It has been reported that at lower temperatures, the carboxylic acid and chitosan create a polyelectrolyte complex, but at temperatures above 100° C. the polyelectrolyte complex converts to an amide bond. K. El-Tahlawy, R. A. Venditti, J. J. Pawlak, *Carbohydrate Polymers*, 2007, 67(3), 319. Higher temperatures improve the properties of the products when reacted within a glass container.

Table 13: Effect of reaction temperature on the absorption, weight loss and strength of SC—C (Reaction conditions: SC:C mass ratio of 1:1, pH=4, Time=3 hours, and Solid:Liquid Ratio of 1:100).

(100° C.) and one that did (120° C.) are included. The water absorption, saline solution (0.9% NaCl) absorption, and tensile strength are all improved for the SC—C relative to the S—C control (as well as starch and chitosan alone), as expected, due to the carboxylic groups in the that form polyelectrolyte complexes with the amino chitosan groups. The maximum degradation temperature of SC—C foam was higher than S—C foam, indicating a more cross linked structure. Interestingly, when the dried SC—C foam was heated at 110° C. for 30 minutes the strength increased significantly, in contrast to the S—C control. This is in agreement with the statement that the salt bonds are converted to covalent amide bonds in the dry curing process for the starch citrate-chitosan material.

Table 14: Properties of S—C, SC—C foams and some related materials. (SC:C mass ratio of 1:1, pH=4, Time=3

TABLE 13

Effect of reaction temperature on the absorption, weight loss and strenght of SC-C (Reaction conditions: SC:C mass ratio of 1:1, pH = 4, Time = 3 hours, and Solid:Liquid Ratio of 1:100).

| Temperature (° C.) | Tensile Strength (N/mm$^2$) | Void fraction | Absorption Time (hr) | Absorption (%) with DI water | | | Absorption (%) with 0.9% NaCl solution | | | Weight loss (%) | |
|---|---|---|---|---|---|---|---|---|---|---|---|
| | | | | Dec | ES | VF | Dec | ES | VF | Water | NaCl |
| 80 | 1.46 | 0.9943 | 0.5 | 3130 | 1280 | 710 | 3360 | 1540 | 1110 | 6.5 | −1.8 |
| 90 | 1.50 | 0.9960 | | 3700 | 1800 | 810 | 4850 | 2120 | 1420 | 3.3 | −5.5 |
| 100 | 1.44 | 0.9963 | | 4170 | 1860 | 1190 | 4900 | 2370 | 1470 | 1.5 | −14.2 |
| 110 | 1.70 | 0.9972 | | 7580 | 2200 | 1360 | 10850 | 2540 | 1980 | 2.1 | −8.6 |
| 120 | 1.81 | 0.9986 | | 10380 | 2450 | 1840 | 12580 | 2810 | 2290 | 3.5 | −7.9 |
| 80 | | | 1.0 | 3520 | 1380 | 830 | 3810 | 1760 | 1680 | 8.7 | −7.1 |
| 90 | | | | 3810 | 1760 | 1690 | 7500 | 2790 | 1760 | 6.1 | −9 |
| 100 | | | | 4480 | 1930 | 1320 | 7780 | 2930 | 1910 | 4.3 | −12.8 |
| 110 | | | | 6490 | 2520 | 1730 | 9040 | 3640 | 2400 | 7.5 | −9.5 |
| 120 | | | | 11310 | 2770 | 1830 | 13960 | 3800 | 2440 | 7.1 | −10.0 |
| 80 | | | 48 | 2490 | 1280 | 740 | 3750 | 1690 | 1500 | 6.1 | −17.6 |
| 90 | | | | 3780 | 1620 | 1290 | 6940 | 3050 | 1960 | 6.7 | −20.7 |
| 100 | | | | 4480 | 1900 | 1390 | 7340 | 3220 | 2190 | 7.1 | −15.7 |
| 110 | | | | 7390 | 2510 | 2030 | 7370 | 3460 | 2270 | 6.8 | −11.2 |
| 120 | | | | 10320 | 2690 | 1980 | 13170 | 3490 | 2190 | 9.2 | −7.8 |

Summary of Cross Linked S—C and SC—C Reaction Results

A summary of properties of the optimized SC—C material relative to several control materials is shown below in Table 14. Both a SC—C that did not require a pressurized vessel hours, (a) T=100° C. or (b) T=120° C. and Material:Liquor Ratio of 1:100. NA means SC, chitosan, or superabsorbent produces a powder, not a foam, and could not be tested. DTG is the maximum peak in rate of mass loss versus temperature in a 10° C./min heating ramp under nitrogen).

TABLE 14

Properties of S-C, SC-C foams and some related materials. (SC:C mass ratio of 1:1, pH = 4, Time = 3 hours, (a) T = 100° C. or (b) T = 120° C. and Material:Liquor Ratio of 1:100. NA means SC, chitosan, or superabsorbent produces a powder, not a foam, and could not be tested. DTG is a maximum peak in rate mass loss verses temperature in a 10° C./min heating ramp under nitrogen).

| Sample | Absorption percent with DI water at 1 hr | | | Absorption percent with 0.9% NaCl at 1 hr | | | Weight Loss (%) at 1 hr | | DTG (° C.) | Residual Char (%) at 600° C. | Tensile strength (N/mm$^2$) | |
|---|---|---|---|---|---|---|---|---|---|---|---|---|
| | Dec | ES | VF | Dec | ES | VF | Water | NaCl | | | Before cure | After cure 110° C., 30 min. |
| SC-C (a) | 4490 | 1940 | 1320 | 6770 | 2430 | 1910 | 4.3 | −12.7 | 306 | 28.7 | 1.4 | 3.5 |
| SC-C (b) | 11320 | 2780 | 1830 | 13970 | 3800 | 2440 | 7.1 | −10.0 | 305 | 25.7 | 1.8 | 4.9 |
| S-C (a) | 2320 | 730 | 530 | 2610 | 720 | 540 | 20.4 | 14.8 | 296 | 21.9 | 1.0 | 1.5 |
| SC | 340 | 120 | 90 | 680 | 130 | 100 | 90.9 | 88.1 | 202 | 32.5 | NA | NA |
| Chitosan | 1170 | 720 | 560 | 1340 | 990 | 550 | 53.0 | 41.0 | 295 | 26.8 | NA | NA |
| Starch | 1020 | 800 | 640 | 930 | 730 | 610 | 23.1 | 16.3 | 315 | 12.5 | 0.0 | 0.0 |
| Commercial Cellulose foam | 730 | 640 | 210 | 760 | 560 | 260 | 55.4 | 50.9 | 270 | 27.2 | 23.8 | 5.8 |
| Super Absorbent | 24120 | 19730 | 14870 | 4730 | 4220 | 1800 | 2.9 | 1.0 | 460 | 50.9 | NA | NA |

With regards to the superabsorbent, the SC—C has significantly lower water absorption but has approximately equivalent saline solution absorption. It is observed in water absorption experiments that the superabsorbent powder expands more than 10 times its original volume whereas the SC—C foam expands approximately to twice its original volume. However, in saline absorption experiments, both the superabsorbent and the SC—C samples expand to twice the original volume. It is important to note that the SC—C is a renewable material whereas the superabsorbent is a synthetic, non-renewable material, and that the environmental aspects of the use of SC—C relative to performance are an important consideration.

In comparison to a renewable commercial cellulose foam sponge, the SC—C demonstrates improved performance in water absorption and saline solution absorption. This indicates that the chemistry introduced into the SC—C enhances the water interaction with the matrix and improves the absorption relative to a simple pore filling mechanism in the commercial cellulose sponge.

Results of Elemental Analysis

As set forth in Table 15 below, elemental analysis shows 7.24% nitrogen in the chitosan. For the repeat unit of chitosan, the nitrogen content ideally should be 14/161 or 8.7%. This indicates that this chitosan is not completely deacetylated. In fact, the manufacturer claims a % deacetylation between 75 and 85%. When the chitosan was blended with starch or SC, the nitrogen % dropped approximately in half, indicating that there are no mass losses accompanying reactions when these materials are blended and reacted.

Table 15: Elemental Analysis of chitosan, S—C, and SC—C. % O calculated by difference.

TABLE 15

Elemental Analysis of chitosan, S-C, and SC-C.

| Sample | % C | % H | % N | % O |
|---|---|---|---|---|
| Chitosan | 40.18 | 7.34 | 7.24 | 45.24 |
| S-C 50/50 w/w | 38.81 | 6.94 | 3.83 | 50.42 |

TABLE 15-continued

Elemental Analysis of chitosan, S-C, and SC-C.

| Sample | % C | % H | % N | % O |
|---|---|---|---|---|
| SC-C 50/50 w/w | 37.35 | 6.40 | 3.70 | 52.55 |

% O calculated by difference.

Results of FTIR Analysis

Figure 18:
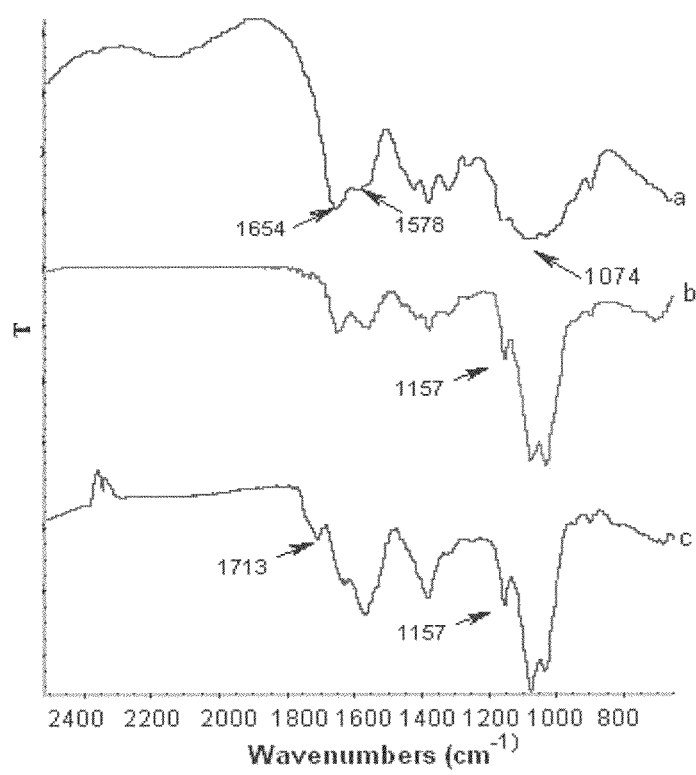
FIG. 18 is a plot of attenuated total reflectance spectra of (a) chitosan; (b) starch-chitosan; and (c) starch citrate-chitosan.

The Attenuated Total Reflectance-Infrared (ATR-IR) spectra of chitosan (a), S—C (b) and SC—C (c) are shown in FIG. 18. The spectrum of chitosan shows that the intensities of the absorbances at 1654 and 1578 cm-1, corresponding to C=O stretching (amide I) and NH-bending (amide II) respectively are lower than that at 1074 cm-1 assigned to —C—O—C— vibration. L. P. Bail, G. F. Morin, H. R. Marchessault, *International J. of Biological Macromolecules*, 1999, 26, 193. However, a new peak observed at 1157 cm-1 (anti-symmetric stretching of the C—O—C bridge) is evident when chitosan is cross linked with S and SC. It is also seen in FIG. 18 that the peak at 1578 cm-1 for chitosan was very weak; conversely, the absorbance peak at 1578 cm-1 for S—C and SC—C was very strong. Besides, another new peak observed at 1713 cm-1 for SC—C indicated the presence of the carboxyl group. Thus, the intensity of amide bands for chitosan increased after SC was incorporated into the chitosan, suggesting that SC was linked to chitosan via reactions between amino groups of chitosan and carboxylic groups of SC. J. Yin, K. L. Kun, X. Chen, V. V. Khutoryanskiy, *Carbohydrate Polymers*, 2006, 63(2), 238.

Results of NMR Analysis

Figure 19A:
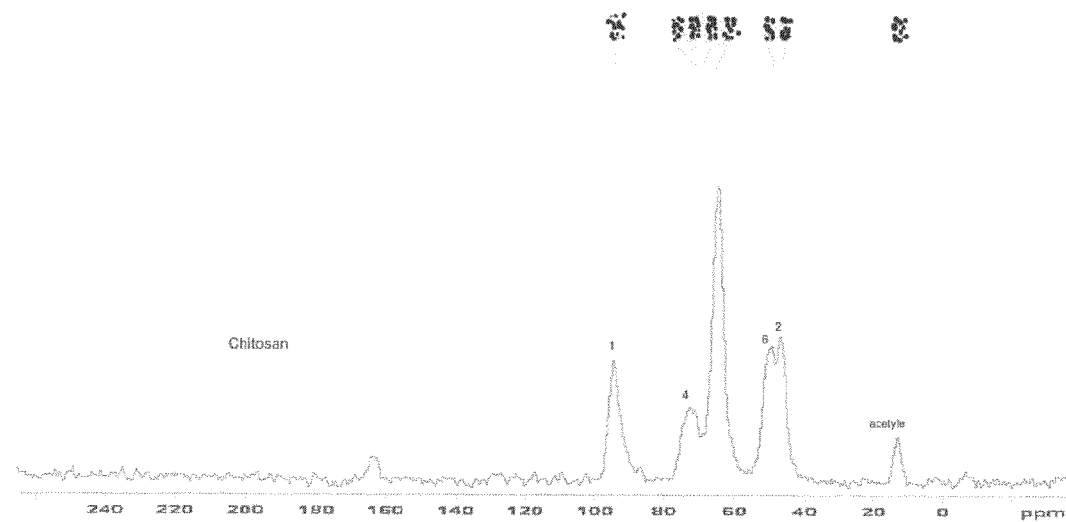
FIG. 19A is a plot of cross polarized magic angle spinning nuclear magnetic resonance spectra for chitosan.
Figure 19B:
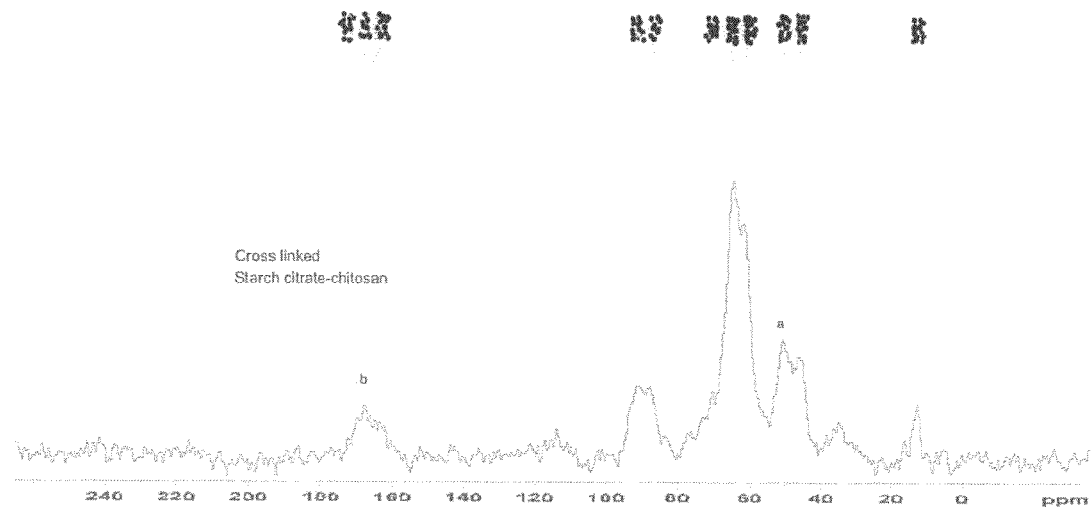
FIG. 19B is a plot of cross polarized magic angle spinning nuclear magnetic resonance spectra for starch citrate-chitosan.

FIG. 19A is a plot of CP: MAS NMR spectra for chitosan. FIG. 19B is a plot of CP: MAS NMR spectra for SC—C. The assignment and chemical shifts of $^{13}$C-NMR (solid state ref.) of chitosan were δ=94.42 (C1), δ=47.01 (C2), δ=64.66 (C3), δ=72.74 (C4), δ=71.41 (C5), δ=49.58 (C6), δ=162.50 (C7, carbonyl carbon on the acetyl group), δ=12.85 (C8, methyl carbon on the acetyl group). For the $^{13}$C-NMR (solid state ref.) of SC—C, new peaks at δ=169.74, 167.53 and 166.09 ppm appeared as three types of carbon signals of a carbonyl group, a carbonyl group of ester (amide) and carbonyl group of carboxyl. This indicates that the carboxyl group of the SC cross linked with amino groups of chitosan. C. Zhang, Q. Ping, H. Zhang, J. Shen, *European Polymer Journal,* 2003, 39, 1629.

The calculation of the degree of deacetylation (Ddeac) of chitosan was as follows:

$$\%Ddeac = \left[1 - \left\{\frac{(\text{Signal intensity due to acetyl group})}{1/6(\text{Signal intensity due to 1, 2, 3, 4, 5, 6})}\right\}\right] \times 100$$

The degree of deacetylation for the chitosan substrate was calculated to be 80.72%. Calculation of the DS of chitosan was as follows:

$$Y = \left\{\frac{1(c-2) \times (\text{Signal intensity due to b})}{6(arom) \times (\text{Signal intensity due to 2})}\right\} \times 100\%$$

The DS was calculated to be 45.43% for the SC derivative. M. R. Thatte, PhD Dissertation, LSU, 2004.

Thermogravimetric Analysis Results

Figure 20A:
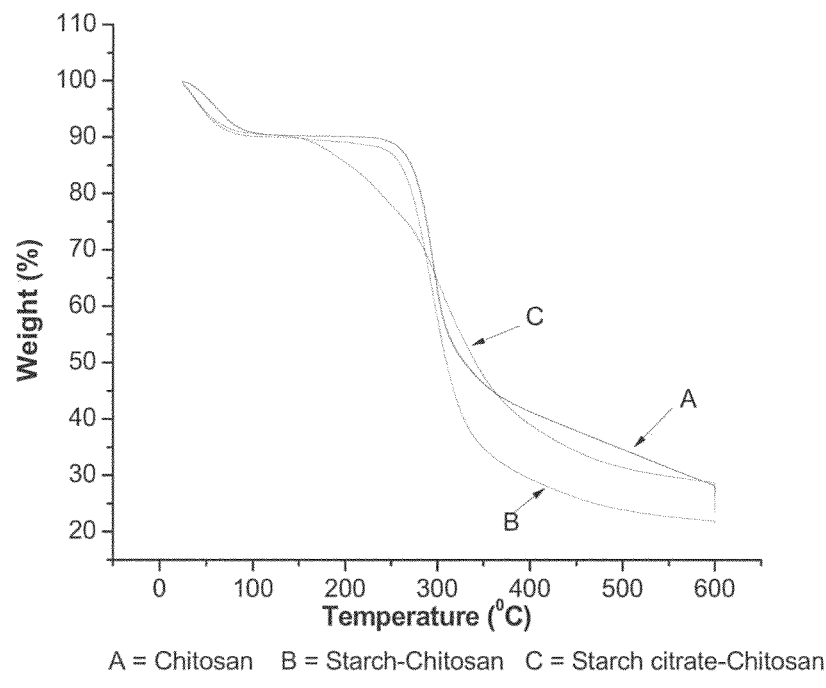
FIG. 20A is a plot of the thermal gravimetric analysis (weight vs. temperature) at a temperature ramp of 10° C./min of chitosan (A); starch-chitosan (B); and starch citrate-chitosan (C).
Figure 20B:
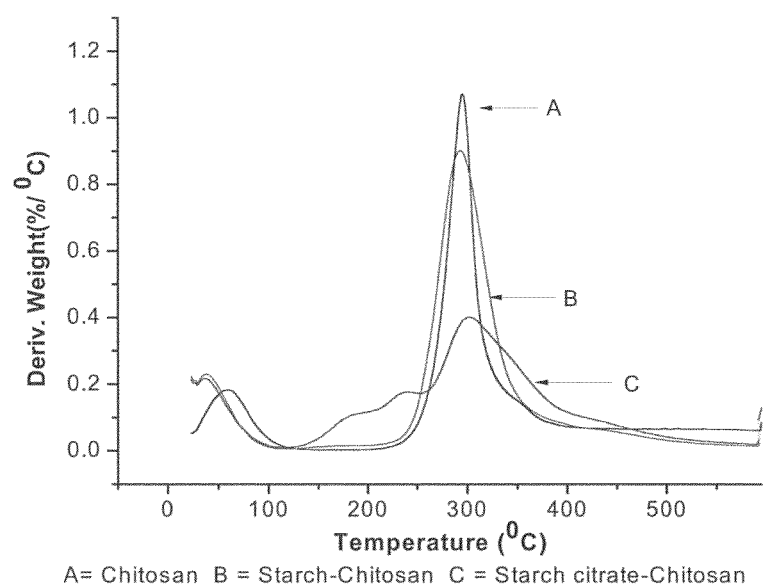
FIG. 20B is a plot of the thermal gravimetric analysis (derivative of weight loss vs. temperature) at a temperature ramp of 10° C./min of chitosan (A); starch-chitosan (B); and starch citrate-chitosan (C).

FIG. 20A is a plot of the thermal gravimetric analysis (weight vs. temperature) at a temperature ramp of 10° C./min of chitosan (A); S—C (B); and SC—C(C). FIG. 20B is a plot of the thermal gravimetric analysis (derivative of weight loss vs. temperature) at a temperature ramp of 10° C./min of chitosan (A); S—C (B); and SC—C(C). For the samples, a weight loss below and around 100° C. was attributed to water evaporation. However, the weight loss above 100° C. was caused by the thermal decomposition of the chitosan, S—C and SC—C based materials. Chitosan had a single sharp decomposition peak at 295° C. in the Differential Themogram (DTG). S—C and SC—C have maximum DTG peaks at 296° C. and 306° C. respectively. The increased DTG peaks and higher char residual indicate an increased cross linking in the SC—C relative to the S—C. The onset of degradation occurs at a much lower temperature for the SC—C, presumably due to the decomposition of the CA plasticizer. CA has a DTG peak at 191° C. with an 82.4% weight loss in the TGA at 210° C. and a 93.5% weight loss at 600° C. (data not shown).

Figure 21:
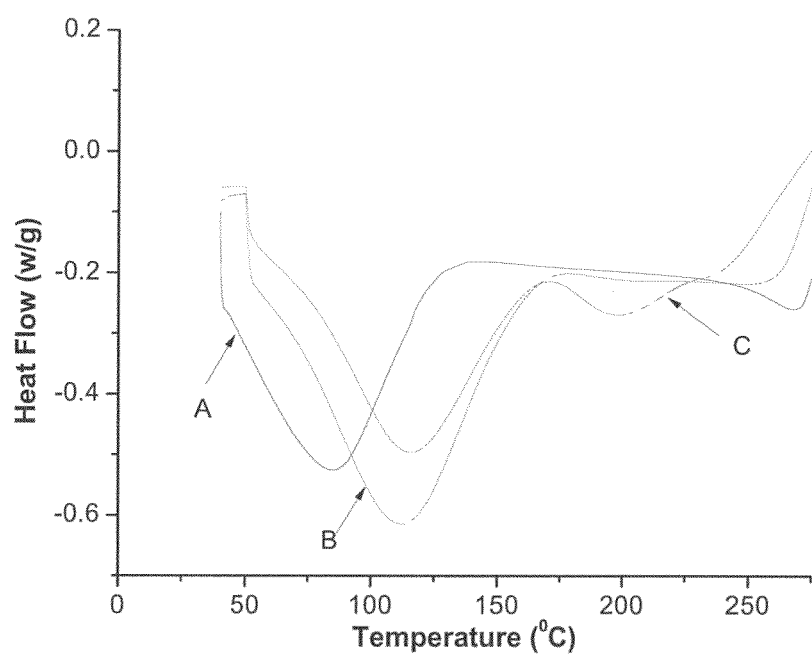
FIG. 21 is a plot of the differential scanning calorimeter curves of chitosan (A), starch-chitosan (B) and starch citrate-chitosan (C) at a 5° C./min heating rate up to 300° C. under nitrogen.

The DSC curves of chitosan, S—C and SC—C at a 5° C./min heating rate up to 300° C. under nitrogen are shown in FIG. 21. All samples show an endothermic peak around 50 to 150° C. indicating water loss. Further, another endothermic peak is observed for starch SC—C at 200° C., in agreement with TGA weight loss that is occurring around 200-300° C. in FIGS. 20A and 20B, and may be attributed to reduced hydrogen bonding as well as the interference of molecular organization due to cross linking. All three materials show the beginning of an exothermic event around 250° C. and above, which correlated to the degradation observed with the TGA. This exotherm starts at a slightly lower temperature for starch citrate-chitosan than the other two samples, similar to the weight loss curves.

Results of DMA

Figure 22:
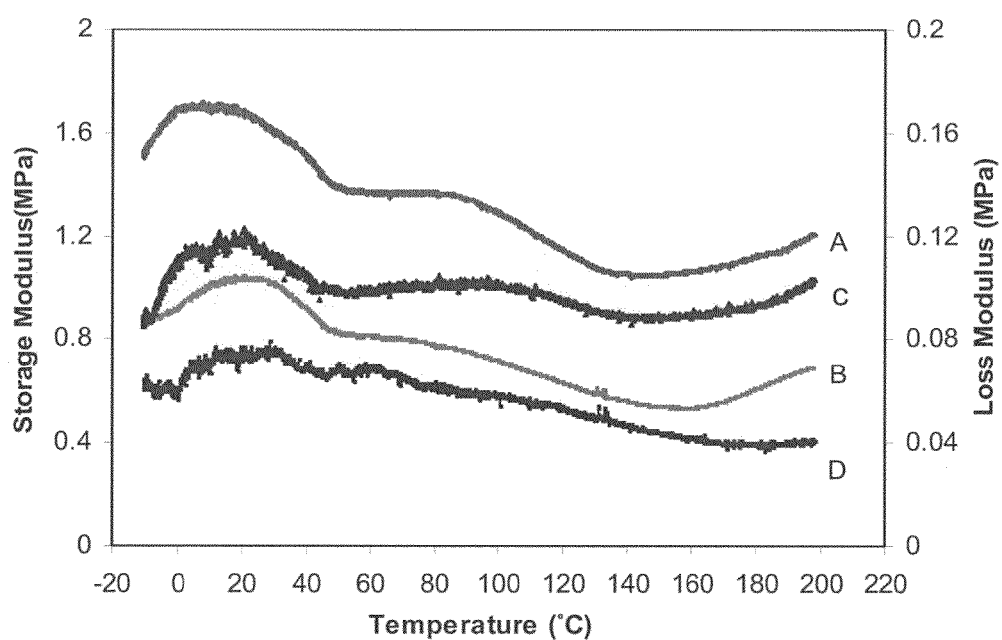
FIG. 22 is a plot of the dynamic mechanical analysis of starch-chitosan and starch citrate-chitosan foams.

Small-strain DMA curves in tension mode of SC—C foam and S—C foam (storage and loss moduli) are shown in FIG. 22. The storage modulus of SC—C and S—C foam both increased with the increased temperature up to 12.5° C. and then decreased. It is also observed from FIG. 22 that the storage modulus of SC—C foam was significantly higher than S—C foam, reflecting increased cross linking. This conclusion does not change when considering that these two materials had different apparent densities; SC—C and S—C had apparent densities of 0.0041 and 0.0076 g/cm$^3$, respectively. Also there is a decrease in loss modulus for SC—C foam from 12.5 to 200° C. of about 13.4% and for S—C foam of about 46.1%. This is in agreement with the increased cross linking in the SC—C relative to the S—C foam.

Results of Dynamic Contact Angle with Water

The dynamic contact angle with DI water at 0.5 seconds was determined to be 110° for S—C foam. The water drop remained unchanged for approximately 30 seconds. In contrast, the dynamic contact angles with DI water at 0.5 seconds for SC—C foam was 0° and the drop was fully absorbed in 0.5 seconds. This reflects the significantly increased absorbency of the SC—C foam relative to the S—C foam. The short time contact angle of water on the S—C is attributed to the roughness of the surface; at longer times, the contact angle is measured as 64° at 72 seconds and 26° at 78 seconds.

Conclusions

SC—C microcellular cross linked foams have been prepared by reacting SC and chitosan in an aqueous medium. Optimum reaction conditions for the SC—C were determined to be 3 hours, 120° C., pH=4, SC:C mass ratio of 1:1, and solid:liquor ratio of 1:100. At these conditions, a minimum mass loss upon immersion in water, high water and saline absorption, and adequate strength was realized. The cross linked SC—C foam has significantly increased water absorption and strength, and decreased weight loss compared to S—C foam. The additional peaks observed in ATR and NMR, the increased strength, higher storage modulus and lower loss modulus are in agreement with the carboxyl group of SC forming a covalent bond with the amino group of chitosan.

EXAMPLE 5

In this Example, experimental results are presented associated with the use of samples of HCC—C and SC—C as chelating agents to remove metals from solution including Pb, Hg, Cd, and As. Samples of Thiol-SAMMS and Sorbatech 450 were also used as chelating agents in this Example for comparison purposes. Table 16 below summarizes the results of Pb, Hg, and Cd chelation, where samples of HCC—C, SC—C, Thiol-SAMMS and Sorbatech 450 were used as the chelating agents.

Table 16: Results of Pb, Hg, and Cd chelation, where samples of HCC—C, SC—C, Thiol-SAMMS and Sorbatech 450 were used as chelating agents.

TABLE 16

Results of Pb, Hg, and Cd chelation, where samples of HCC-C, SC-C, Thiol-SAMMS and Sorbatech 450 were used as chelating agents.

| Sample | Heavy Metal | Initial Concentration (µg/L) | Final Concentration (µg/L) | Metal Loading (mg/g) |
|---|---|---|---|---|
| HCC-C | Pb | 2185850 | 946150 | 247.938 |
|  | Hg | 200000 | 70205 | 51.918 |
|  | Cd | 302940 | 224400 | 31.416 |
| SC-C | Pb | 2185850 | 935800 | 250.01 |
|  | Hg | 200000 | 80235 | 47.906 |
|  | Cd | 302940 | 201960 | 40.392 |
| Thiol-SAMMS | Pb | 3040 | 300 | 0.2740 |
|  | Hg | 487 | 0 | 1.0146 |
|  | Cd | 4670 | 32 | 0.4638 |
| Sorbatech 450 | Pb | 2185850 | 2020100 | 35.223 |
|  | Hg | 100000 | 20090 | 31.964 |
|  | Cd | 302940 | 258060 | 17.952 |

Pb Chelation

A Pb standard solution (0.01M) was provided. Samples of HCC—C, SC—C, Thiol-SAMMS and Sorbatech 450 were each added to separate 20 ml samples of Pb solution. EDTA (0.01M) was used as the titrant. As can be seen in Table 16, Pb metal loading associated with the HCC—C and SC—C samples was significantly higher than in the Thiol-SAMMS and Sorbatech 450 samples.

Hg Chelation

An Hg standard solution (1000 mg/L) was provided. Samples of HCC—C, SC—C and Thiol-SAMMS were each added to separate 40 ml samples of Hg solution. Sorbatech 450 was added to a 20 ml sample of Hg solution. $PbNO_3$ (0.02M) was used as the titrant. As can be seen in Table 16, Hg metal loading associated with the HCC—C and SC—C samples was significantly higher than in the Thiol-SAMMS and Sorbatech 450 samples.

Cd Chelation

A Cd standard solution (1000 mg/L) was provided. Samples of HCC—C, SC—C, Thiol-SAMMS and Sorbatech 450 were each added to separate 20 ml samples of Cd solution. $PbNO_3$ (0.02M) was used as the titrant. As can be seen in Table 16, Cd metal loading associated with the HCC—C and SC—C samples was significantly higher than in the Thiol-SAMMS and Sorbatech 450 samples.

As Chelation

Table 17 below summarizes the results of As chelation, where samples of HCC—C, SC—C, Sorbatech 450, Lanert, Purolite, and Absorbia GTO were used as the chelating agents. A 0.025 g sample of HCC—C was placed in an As solution (50 ml, with an initial As concentration of 50100 µg/L) for six minutes. The same experiment was carried out with an As solution having an initial concentration of 5000 µg/L. These same experiments (or experiments with slightly varying initial concentrations of As, as shown in Table 17) were carried out with SC—C, as well as the other chelating agents shown in Table 17. As shown in Table 17, HCC—C and SC—C performed similarly to Sorbatech 450 in removing As from the As solution with an initial concentration of 50000 µg/L. With respect to the As solutions having initial concentrations of either 4950 or 5000 µg/L, the addition of the HCC—C and SC—C samples both provided for significantly lower final As concentrations than the other chelating agents.

Table 17: Results of As chelation, where samples of HCC—C, SC—C, Sorbatech 450, Lanert, Alumina, Purolite and Absorbia GTP were used as chelating agents.

TABLE 17

Results of As chelation, where samples of HCC-C, SC-C, Sorbatech 450, Lanert, Alumina, Purolite and Absorbia GTP were used as chelating agents.

| Sample | Metal | Initial Concentration (µg/L) | Final Concentration (µg/L) |
|---|---|---|---|
| HCC-C | As | 50100 | 45700 |
| SC-C | As | 50100 | 45400 |
| Sorbatech 450 | As | 50100 | 45600 |
| HCC-C | As | 5000 | 4310 |
| SC-C | As | 5000 | 4030 |
| Sorbatech 450 | As | 4950 | 4900 |
| Lanert | As | 4950 | 4750 |
| Alumina | As | 4950 | 4710 |
| Purolite | As | 4950 | 4680 |
| Absorbia GTO | As | 4950 | 4930 |

It will be understood that various aspects or details of the invention may be changed without departing from the scope of the invention. Furthermore, the foregoing description is for the purpose of illustration only, and not for the purpose of limitation the invention being defined by the claims.

What is claimed is:

1. A composition of matter, comprising:
   chitosan; and
   a modified carbohydrate, wherein the modified carbohydrate has been modified so as to have an increased carboxyl content as compared to an unmodified counterpart carbohydrate, and wherein a carboxyl group of the modified carbohydrate is covalently bonded with an amino group of the chitosan, and wherein the composition of matter comprises a cross linked starch citrate-chitosan compound.

2. The composition of matter according to claim 1, wherein the increased carboxyl content of the modified carbohydrate is introduced by a cross linking agent comprising at least one of citric acid, succinic anhydride, maleic anhydride and sodium monochloroacetate.

3. The composition of matter according to claim 1, wherein the composition of matter has a tensile strength of about 0.10 to about 1.81 $N/mm^2$.

4. The composition of matter according to claim 1, wherein the composition of matter has a void fraction of about 0.9446 to about 0.9986.

5. The composition of matter according to claim 1, wherein the composition of matter has a degradation temperature of about 305° C. to about 306° C.

6. A composition of matter, comprising:
   chitosan; and
   a modified carbohydrate, wherein the modified carbohydrate has been modified so as to have an increased carboxyl content as compared to an unmodified counterpart carbohydrate, and wherein a carboxyl group of the modified carbohydrate is covalently bonded with an amino group of the chitosan, and wherein the modified carbohydrate comprises hemicellulose and the hemicellulose has a carboxyl content of greater than 352 mequ/100 grams.

7. The composition of matter according to claim 6, wherein the composition of matter comprises a cross linked hemicellulose citrate-chitosan compound.

8. The composition of matter according to claim 7, wherein the composition of matter has a tensile strength of about 0.20 to about 1.61 $N/mm^2$.

9. The composition of matter according to claim 7, wherein the composition of matter has a void fraction of about 0.9735 to about 0.9980.

10. The composition of matter according to claim 7, wherein the composition of matter has a degradation temperature of about 296° C.

11. The composition of matter according to claim 6, wherein the increased carboxyl content of the modified carbohydrate is introduced by a cross linking agent comprising at least one of citric acid, succinic anhydride, maleic anhydride and sodium monochloroacetate.

12. The composition of matter according to claim 6, wherein the hemicellulose has a carboxyl content in a range of 352 mequ/100 grams to 742 mequ/100 grams.

13. A composition of matter, comprising:
   chitosan; and
   a modified carbohydrate, wherein the modified carbohydrate has been modified so as to have an increased carboxyl content as compared to an unmodified counterpart carbohydrate, and wherein a carboxyl group of the modified carbohydrate is covalently bonded with an amino group of the chitosan, and wherein the modified carbohydrate comprises starch and the starch has a carboxyl content of about 180 mequ/100 grams or greater.

14. The composition of matter according to claim 13, wherein the increased carboxyl content of the modified carbohydrate is introduced by a cross linking agent comprising at least one of citric acid, succinic anhydride, maleic anhydride and sodium monochloroacetate.

15. The composition of matter according to claim 13, wherein the starch has a carboxyl content in a range of 180 mequ/100 grams to 473 mequ/100 grams.

16. A composition of matter, comprising:
chitosan; and
a modified carbohydrate, wherein the modified carbohydrate has been modified so as to have an increased carboxyl content as compared to an unmodified counterpart carbohydrate, and wherein a carboxyl group of the modified carbohydrate is covalently bonded with an amino group of the chitosan, wherein the composition of matter comprises a cross linked modified carbohydrate-chitosan compound, and wherein the modified carbohydrate has a degree of esterification of 17% or greater.

17. The composition of matter according to claim 16, wherein the modified carbohydrate comprises a carbohydrate component comprising at least one of hemicellulose and starch.

18. The composition of matter according to claim 16, wherein the increased carboxyl content of the modified carbohydrate is introduced by a cross linking agent comprising at least one of citric acid, succinic anhydride, maleic anhydride and sodium monochloroacetate.

19. The composition of matter according to claim 16, wherein the modified carbohydrate has a degree of esterification in a range of 17% to 46.6%.

20. A method of making the cross linked starch citrate-chitosan compound according to claim 1, the method comprising:
providing an aqueous citric acid solution including citric acid, water and a catalyst;
reacting a starch component with the citric acid solution to provide a starch citrate solution; and
mixing the starch citrate solution with a chitosan solution including chitosan, water and a weak acid to produce the cross linked starch citrate-chitosan compound.

21. The method of claim 20, further comprising freeze drying the cross linked starch citrate-chitosan compound to form a foam.

22. The method of claim 21, further comprising curing the foam by heating the foam at a predetermined temperature for a predetermined time to increase the tensile strength of the foam.

23. A method of making the composition of matter according to claim 6, the method comprising:
providing an aqueous citric acid solution including citric acid, water and a catalyst;
reacting a hemicellulose component with the citric acid solution to provide a hemicellulose citrate solution; and
mixing the hemicellulose citrate solution with a chitosan solution including chitosan, water and a weak acid to produce a cross linked hemicellulose citrate-chitosan compound.

24. The method of claim 23, further comprising freeze drying the cross linked hemicellulose citrate-chitosan to form a foam.

25. The method of claim 24, further comprising curing the foam by heating the foam at a predetermined temperature for a predetermined time to increase the tensile strength of the foam.

26. A method of making the cross linked modified carbohydrate-chitosan compound according to claim 16, the method comprising:
esterifying a carbohydrate component by combining the carbohydrate component with a cross linking agent in an aqueous solution, wherein a mixture including the carbohydrate component and the cross linking agent is formed thereby;
dehydrating the mixture to form the modified carbohydrate; and
cross linking the modified carbohydrate with chitosan by reacting the modified carbohydrate with chitosan under aqueous conditions, thereby forming a cross linked modified carbohydrate-chitosan compound.

27. The method of claim 26, wherein esterifying the carbohydrate component further comprises adding a catalyst to the aqueous solution.

28. The method of claim 27, wherein the catalyst is selected from the group consisting of sodium hypophosphite, sodium bisulfate and sodium bisulfite.

29. The method of claim 26, further comprising removing the cross linked modified carbohydrate-chitosan compound from the cross linking reaction mixture.

30. The method of claim 26, further comprising freeze drying the cross linked carbohydrate-chitosan compound to form a foam.

31. The method of claim 26, wherein the carbohydrate component is selected from the group consisting of hemicellulose and starch.

32. The method of claim 26, wherein the cross linking agent is selected from the group consisting of citric acid, sodium monochloroacetate, maleic anhydride and succinic anhydride.

33. The method of claim 26, wherein cross linking the modified carbohydrate with chitosan is carried out at a temperature of about 80° C. to about 120° C.

34. The method of claim 26, wherein cross linking the modified carbohydrate with chitosan is carried out at a solid to liquid ratio of at least 1:100.

35. The method of claim 26, wherein cross linking the modified carbohydrate with chitosan is carried out at a pH of about 3 to about 6.

36. The method of claim 26, wherein cross linking the modified carbohydrate with chitosan is carried out at a mass ratio of the modified carbohydrate to chitosan of about 0.4:1 to about 1.2:1.

37. A water absorption process which comprises contacting water with the cross linked modified carbohydrate-chitosan compound according to claim 16.

38. A metal chelation process which comprises contacting a solution containing a metal with the cross linked modified carbohydrate-chitosan compound according to claim 16.

39. The metal chelation process of claim 38, wherein the metal is selected from the group consisting of Pb, Hg, Cd and As.

40. A salt absorption process which comprises contacting a solution containing salt with the cross linked modified carbohydrate-chitosan compound according to claim 16.

* * * * *